(12) United States Patent
Sundermann et al.

(10) Patent No.: US 7,786,328 B2
(45) Date of Patent: Aug. 31, 2010

(54) CYCLOHEXYL-1,4-DIAMINE COMPOUNDS

(75) Inventors: Corinna Sundermann, Aachen (DE); Bernd Sundermann, Aachen (DE)

(73) Assignee: Gruenenthal GmbH, Aachen (DE)

( * ) Notice: Subject to any disclaimer, the term of this patent is extended or adjusted under 35 U.S.C. 154(b) by 38 days.

(21) Appl. No.: 11/594,953

(22) Filed: Nov. 9, 2006

(65) Prior Publication Data

US 2007/0281954 A1  Dec. 6, 2007

Related U.S. Application Data

(63) Continuation of application No. PCT/EP2005/004912, filed on May 6, 2005.

(30) Foreign Application Priority Data

May 10, 2004 (DE) ............... 10 2004 023 506

(51) Int. Cl.
*C07C 235/64* (2006.01)
*C07C 233/79* (2006.01)
*C07D 333/20* (2006.01)
*A61K 31/167* (2006.01)
*A61K 31/381* (2006.01)

(52) U.S. Cl. ..................... 564/123; 514/274

(58) Field of Classification Search ............... None
See application file for complete search history.

(56) References Cited

U.S. PATENT DOCUMENTS

| | | | |
|---|---|---|---|
| 4,656,182 A | 4/1987 | Horwell | |
| 7,348,354 B2 * | 3/2008 | Hinze et al. | 514/419 |
| 2004/0019058 A1 * | 1/2004 | Bridger et al. | 514/249 |
| 2005/0245593 A1 | 11/2005 | Sundermann et al. | |
| 2005/0261358 A1 | 11/2005 | Hinze et al. | |

FOREIGN PATENT DOCUMENTS

| | | |
|---|---|---|
| DE | 102 52 650 A1 | 5/2004 |
| EP | 0 147 085 B1 | 3/1990 |
| WO | WO 02/089783 A1 | 11/2002 |
| WO | WO 02/090317 A1 | 11/2002 |
| WO | WO 02/090330 A1 | 11/2002 |
| WO | WO 2004/043899 A1 | 5/2004 |
| WO | WO 2004/043909 A1 | 5/2004 |
| WO | WO 2004043899 A1 * | 5/2004 |
| WO | WO 2004043909 A1 * | 5/2004 |
| WO | WO 2005/070407 A1 | 8/2005 |
| WO | WO 2005070407 A1 * | 8/2005 |

OTHER PUBLICATIONS

International Search Reports dated Mar. 17, 2004 and Oct. 6, 2005 with the English translation of the relevant portion (Eight (8) Pages).
German Search Report dated Oct. 22, 2004 with English translation (Seven (7) Pages).

* cited by examiner

*Primary Examiner*—Daniel M Sullivan
*Assistant Examiner*—Yevegeny Valenrod
(74) *Attorney, Agent, or Firm*—Crowell & Moring LLP

(57) ABSTRACT

Novel cyclohexyl-1,4-diamine compounds corresponding to formula I

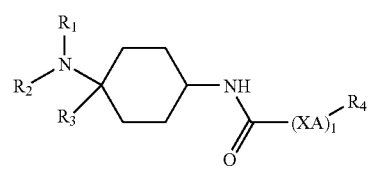

processes for preparing such compounds, pharmaceutical formulations comprising these compounds, methods of making such pharmaceutical formulations and the related methods of treating or inhibiting certain conditions or disorders.

22 Claims, No Drawings

CYCLOHEXYL-1,4-DIAMINE COMPOUNDS

CROSS-REFERENCE TO RELATED APPLICATIONS

This application is a continuation of International patent application Serial No. PCT/EP2005/004912 filed May 6, 2005 which claims benefit to German patent application Serial No. 10 2004 023 506.6 filed May 10, 2004, the entire disclosures of which are hereby incorporated in their entirety.

FIELD OF THE INVENTION

The present invention relates to cyclohexyl-1,4-diamine compounds, processes for preparing such compounds, pharmaceutical formulations comprising these compounds, methods of making such pharmaceutical formulations and the related methods of treating or inhibiting certain conditions or disorders.

BACKGROUND OF THE INVENTION

The treatment of chronic and non-chronic states of pain is of great importance in medicine. There is a worldwide need for pain therapies which are highly effective. The urgent need for action for targeted treatment of chronic and non-chronic states of pain appropriate for the patient, by which is to be understood successful and satisfactory pain treatment for the patient, is documented in the large number of scientific works which have been published recently in the field of applied analgesics and of basic research into nociception.

Conventional μ-opioids, such as morphine, have a good action in the therapy of severe to very severe pain and are of very great importance for pain therapy. However, it may be of advantage if, in addition to the μ-opioid receptor, other opioid receptors, in particular the ORL1 receptor, are influenced since pure μ-opioids also have undesirable side effects, such as constipation and respiratory depression, and can also lead to dependency. The δ, κ and ORL1 opioid receptors are also involved in the pain event (Opioids: Introduction, p. 127-150, Further Opioid Receptors, 455-476 in: Analgesics—From Chemistry and Pharmacology to Clinical Application, Wiley VCH, 2002).

It is moreover known that influencing of the reuptake of serotonin and/or noradrenaline can have a favourable effect on the action spectrum and spectrum of side effects of opioids (example: tramadol, cf. Opioids with Clinical Relevance: Tramadol, 228-230 in: Analgesics—From Chemistry and Pharmacology to Clinical Application, Wiley VCH 2002).

The ORL1 receptor is moreover also involved in regulation of further physiological and pathophysiological processes. These include, inter alia, learning and memory development (Manabe et al., Nature, 394, 1997, p. 577-581), audition (Nishi et al., EMBO J., 16, 1997, p. 1858-1864) and numerous further processes. A review article by Calo et al. (Br. J. Pharmacol., 129, 2000, 1261-1283) gives an overview of the indications or biological processes in which the ORL1 receptor plays a role or with high probability could play a role. There are mentioned, inter alia: analgesia, stimulation and regulation of food intake, influence on μ-agonists, such as morphine, treatment of withdrawal symptoms, reduction in the addiction potential of opioids, anxiolysis, modulation of movement activity, memory impairments, epilepsy; modulation of neurotransmitter secretion, in particular of glutamate, serotonin and dopamine, and therefore neurodegenerative diseases; influencing of the cardiovascular system, initiation of an erection, diuresis, antinatriuresis, electrolyte balance, arterial blood pressure, water retention diseases, intestinal motility (diarrhea), relaxing effects on the respiratory tract, micturition reflex (urinary incontinence). The use of agonists and antagonists as anoretics, analgesics (also in co-administration with opioids) or nootropics is also discussed.

Structurally related compounds which have an affinity for the ORL1 receptor are known from the prior art (WO 02090317). No influence on the reuptake of noradrenaline and serotonin has hitherto been described for this structure class.

SUMMARY OF THE INVENTION

The object of the present invention was to provide medicaments which act on the opioid receptor system and are therefore suitable for medicaments, in particular for treatment of the various diseases associated with this system according to the prior art, and for use in the indications mentioned there. The compounds should furthermore influence the reuptake of noradrenaline and serotonin.

The invention therefore provides substituted cyclohexyl-1,4-diamine derivatives of the general formula I

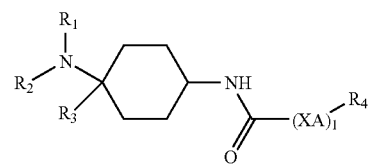

wherein $R^1$ and $R^2$ independently of one another represent H; $C_{1-5}$-alkyl, in each case saturated or unsaturated, branched or unbranched, mono- or polysubstituted or unsubstituted; $C_{3-8}$-cycloalkyl, in each case mono- or polysubstituted or unsubstituted; or aryl, $C_{3-8}$-cycloalkyl or heteroaryl bonded via $C_{1-3}$-alkyl and in each case mono- or polysubstituted or unsubstituted;

or the radicals $R^1$ and $R^2$ together represent $CH_2CH_2OCH_2CH_2$, $CH_2CH_2NR^{10}CH_2CH_2$ or $(CH_2)_{3-6}$, wherein $R^{10}$ denotes H; $C_{1-5}$-alkyl, in each case saturated or unsaturated, branched or unbranched, mono- or polysubstituted or unsubstituted; $C_{3-8}$-cycloalkyl, in each case mono- or polysubstituted or unsubstituted; aryl or heteroaryl, in each case mono- or polysubstituted or unsubstituted; or aryl, $C_{3-8}$-cycloalkyl or heteroaryl bonded via $C_{1-3}$-alkyl and in each case mono- or polysubstituted or unsubstituted; C(O)phenyl, C(O)heteroaryl, $C(O)C_{1-5}$-alkyl, in each case substituted or unsubstituted;

$R^3$ represents $C_{1-5}$-alkyl, in each case saturated or unsaturated, branched or unbranched, mono- or polysubstituted or unsubstituted; $C_{3-8}$-cycloalkyl, in each case mono- or polysubstituted or unsubstituted; aryl or heteroaryl, in each case unsubstituted or mono- or polysubstituted; aryl, heteroaryl or $C_{3-8}$-cycloalkyl bonded via $C_{1-3}$-alkyl and in each case unsubstituted or mono- or polysubstituted;

X represents $(C^5R^6)_n$; aryl or heteroaryl, in each case unsubstituted or mono- or polysubstituted and in each case also bridged via a $C_{1-3}$-alkyl chain, which can be substituted; where n=0, 1, 2, 3 or 4;

A represents NH, ON, where in this case the bond between N and $R^4$ is a double bond, O or S, l represents 1 or 2;

$R^4$ represents $C_{1-5}$-alkyl, in each case saturated or unsaturated, branched or unbranched, mono- or polysubstituted or unsubstituted; $C_{3-8}$-cycloalkyl, in each case mono- or polysubstituted or unsubstituted; aryl or heteroaryl, in each case mono- or polysubstituted or unsubstituted; or aryl, $C_{3-8}$-cycloalkyl or heteroaryl bonded via $C_{1-3}$-alkyl and in each case mono- or polysubstituted or unsubstituted;

$R^5$ and $R^6$ independently of one another represent H, $C_{1-5}$-alkyl, in each case saturated or unsaturated, branched or unbranched, mono- or polysubstituted or unsubstituted; aryl, in each case mono- or polysubstituted or unsubstituted, with the proviso that X does not denote heteroaryl if l represents 1 and at the same time A represents O or S;

in the form of the racemate; the enantiomers, diastereomers, mixtures of the enantiomers or diastereomers or an individual enantiomer or diastereomer; the bases and/or salts of physiologically acceptable acids or cations or in the form of its solvates, in particular the hydrates thereof.

If a radical, for example X, can occur twice within one compound, it can also assume different meanings.

The compounds according to the invention show good binding to the μ receptor and the ORL1 receptor, and also to other opioid receptors. It has been found, surprisingly, that the compounds are also good inhibitors of the reuptake of noradrenaline and serotonin. They are therefore also suitable for treatment of depressions and/or bulimia and/or anorexia and/or catalepsy and/or for anxiolysis and/or for increasing vigilance and/or libido.

The terms "$C_{1-5}$-alkyl" and "$C_{1-3}$-alkyl" in the context of this invention include acyclic saturated or unsaturated hydrocarbon radicals, which can be branched-chain or straight-chain and unsubstituted or mono- or polysubstituted, having 1, 2, 3, 4 or 5 C atoms or, respectively, 1, 2 or 3 C atoms, i.e. $C_{1-5}$-alkanyls, $C_{2-5}$-alkenyls and $C_{2-5}$-alkynyls or, respectively, $C_{1-3}$-alkanyls, $C_{2-3}$-alkenyls and $C_{2-3}$-alkynyls. In this context, alkenyls have at least one C—C double bond and alkynyls have at least one C—C triple bond. Alkyl is advantageously chosen from the group which includes methyl, ethyl, n-propyl, 2-propyl, n-butyl, iso-butyl, sec-butyl, tert-butyl, n-pentyl, iso-pentyl, neo-pentyl, ethylenyl (vinyl), ethynyl, propenyl (—CH$_2$CH=CH$_2$, —CH=CH—CH$_3$, —C(=CH$_2$)—CH$_3$), propynyl (—CH—CH≡CH, —C≡C—CH$_3$), 1,1-dimethylethyl, 1,1-dimethylpropyl, butenyl, butynyl, pentenyl and pentynyl.

The term "cycloalkyl" or "$C_{3-8}$-cycloalkyl" for the purpose of this invention denotes cyclic hydrocarbons having 3, 4, 5, 6, 7 or 8 carbon atoms, it being possible for the hydrocarbons to be saturated or unsaturated (but not aromatic), unsubstituted or mono- or polysubstituted. In respect of cycloalkyl, the expression also includes saturated or unsaturated (but not aromatic) cycloalkyls in which one or two carbon atoms are replaced by a heteroatom S, N or O. $C_{3-8}$-Cycloalkyl is advantageously chosen from the group which contains cyclopropyl, cyclobutyl, cyclopentyl, cyclohexyl, cycloheptyl, cyclooctyl, cyclopentenyl, cyclohexenyl, cycloheptenyl and cyclooctenyl, and also tetrahydropyranyl, dioxanyl, dioxolanyl, morpholinyl, piperidinyl, piperazinyl, pyrazolinonyl and pyrrolidinyl.

The expression (CH$_2$)$_{3-6}$ is to be understood as meaning —CH$_2$—CH$_2$—CH$_2$—, —CH$_2$—CH$_2$—CH$_2$—CH$_2$—, —CH$_2$—CH$_2$—CH$_2$—CH$_2$—CH$_2$— and —CH$_2$—CH$_2$—CH$_2$—CH$_2$—CH$_2$—CH$_2$—.

The term "aryl" in the context of this invention denotes carbocyclic ring systems having at least one aromatic ring but without heteroatoms in only one of the rings, inter alia phenyls, naphthyls and phenanthrenyls, fluoranthenyls, fluorenyls, indanyls and tetralinyls. The aryl radicals can also be fused with further saturated, (partly) unsaturated or aromatic ring systems. Each aryl radical can be unsubstituted or mono- or polysubstituted, it being possible for the substituents on the aryl to be identical or different and in any desired and possible position of the aryl. Phenyl or naphthyl radicals are particularly advantageous.

The term "heteroaryl" represents a 5-, 6- or 7-membered cyclic aromatic radical which contains at least 1, optionally also 2, 3, 4 or 5 heteroatoms, the heteroatoms being identical or different and it being possible for the heterocyclic radical to be unsubstituted or mono- or polysubstituted; in the case of substitution on the heterocyclic radical, the substituents can be identical or different and can be in any desired and possible position of the heteroaryl. The heterocyclic radical can also be part of a bi- or polycyclic system. Preferred heteroatoms are nitrogen, oxygen and sulfur. It is preferable for the heteroaryl radical to be chosen from the group which contains pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl, isothiazolyl, triazolyl, triazinyl, quinazolinyl, carbazolyl, phenazinyl, phenothiazinyl or oxadiazolyl, it being possible for the bond to the compounds of the general structure I to be via any desired and possible ring member of the heteroaryl radical.

In connection with "alkyl", the expression "substituted" in the context of this invention is understood as meaning replacement of one or more hydrogen radicals by F, Cl, Br, I, —CN, =O, =S, NH$_2$, NH-alkyl, NH-aryl, NH-heteroaryl, NH-cycloalkyl, NH-alkyl-aryl, NH-alkyl-heteroaryl, NH-alkyl-OH, N(alkyl)$_2$, N(alkyl-aryl)$_2$, N(alkyl-heteroaryl)$_2$, N(cycloalkyl)$_2$, N(alkyl-OH)$_2$, NH(C=O)alkyl, NH(C=O)aryl, NO$_2$, SH, S-alkyl, S-aryl, S-heteroaryl, S-alkyl-aryl, S-alkyl-heteroaryl, S-cycloalkyl, S-alkyl-OH, S-alkyl-SH, OH, O-alkyl, O-aryl, O-heteroaryl, O-alkyl-aryl, O-alkyl-heteroaryl, O-cycloalkyl, O-alkyl-OH, CHO, C(=O)C$_{1-6}$-alkyl, C(=S)C$_{1-6}$-alkyl, C(=O)aryl, C(=S)aryl, C(=O)C$_{1-6}$-alkyl-aryl, C(=S)C$_{1-6}$-alkyl-aryl, C(=O)-heteroaryl, C(=S)-heteroaryl, C(=O)-cycloalkyl, C(=S)-cycloalkyl, CO$_2$H, CO$_2$-alkyl, CO$_2$-alkyl-aryl, C(=O)NH$_2$, C(=O)NH-alkyl, C(=O)NHaryl, C(=O)NH-cycloalkyl, C(=O)N(alkyl)$_2$, C(=O)N(alkyl-aryl)$_2$, C(=O)N(alkyl-heteroaryl)$_2$, C(=O)N(cycloalkyl)$_2$, SO-alkyl, SO$_2$-alkyl, SO$_2$NH$_2$, SO$_3$H, PO(O—C$_{1-6}$-alkyl)$_2$, cycloalkyl, aryl or heteroaryl, polysubstituted radicals being understood as meaning those radicals which are substituted several times, e.g. two or three times, either on different or on the same atoms, for example three times on the same C atom, as in the case of CF$_3$ or —CH$_2$CF$_3$, or at different places, as in the case of —CH(OH)—CH=CH—CHCl$_2$. Polysubstitution can be with the same or with different substituents. A substituent can also optionally be substituted in its turn; thus —Oalkyl, inter alia, also includes —O—CH$_2$—CH$_2$—O—CH$_2$—CH$_2$—OH.

In respect of "aryl", "heteroaryl" and "cycloalkyl", in the context of this invention "mono- or polysubstituted" is understood as meaning replacement, once or several times, e.g. two, three, four or five times, of one or more hydrogen atoms of the ring system by F, Cl, Br, I, CN, NH$_2$, NH-alkyl, NH-aryl, NH-heteroaryl, NH-alkyl-aryl, NH-alkyl-heteroaryl, NH-cycloalkyl, NH-alkyl-OH, N(alkyl)$_2$, N(alkyl-aryl)$_2$, N(alkyl-heteroaryl)$_2$, N(cycloalkyl)$_2$, N(alkyl-OH)$_2$, NO$_2$, SH, S-alkyl, S-cycloalkyl, S-aryl, S-heteroaryl, S-alkyl-aryl, S-alkyl-heteroaryl, S-cycloalkyl, S-alkyl-OH, S-alkyl-SH, OH, O-alkyl, O-cycloalkyl, O-aryl, O-heteroaryl, O-alkyl-aryl, O-alkyl-heteroaryl, O-cycloalkyl, O-alkyl-OH, CHO, C(=O)$C_{1-6}$-alkyl, C(=S)$C_{1-6}$-alkyl, C(=O)aryl, C(=S)aryl, C(=O)—$C_{1-6}$-alkyl-aryl, C(=S)$C_{1-6}$-alkyl-aryl, C(=O)-heteroaryl, C(=S)-heteroaryl, C(=O)-cycloalkyl, C(=S)-cycloalkyl, $CO_2H$, $CO_2$-alkyl, $CO_2$-alkyl-aryl, C(=O)$NH_2$, C(=O)NH-alkyl, C(=O)NHaryl, C(=O)NH-cycloalkyl, C(=O)N(alkyl)$_2$, C(=O)N(alkyl-aryl)$_2$, C(=O)N(alkyl-heteroaryl)$_2$, C(=O)N(cycloalkyl)$_2$, S(O)-alkyl, S(O)-aryl, $SO_2$-alkyl, $SO_2$-aryl, $SO_2NH_2$, $SO_3H$, $CF_3$, =O, =S; —O—$CH_2$—$CH_2$—O—; alkyl, cycloalkyl, aryl and/or heteroaryl; on one or optionally different atoms (it being possible for a substituent optionally to be substituted in its turn). Polysubstitution here is with the same or with different substituents.

The expression salt is to be understood as meaning any form of the active compound according to the invention in which this assumes an ionic form or is charged and is coupled with a counter-ion (a cation or anion) or is in solution. This is also to be understood as meaning complexes of the active compound with other molecules and ions, in particular complexes which are complexed via ionic interactions. In particular, by these there are understood (and this is also a preferred embodiment of this invention) physiologically acceptable salts, in particular physiologically acceptable salts with cations or bases and physiologically acceptable salts with anions or acids or also a salt formed with a physiologically acceptable acid or a physiologically acceptable cation.

In the context of this invention, the expression of physiologically acceptable salt with anions or acids is understood as meaning at least one of the compounds according to the invention—usually protonated, for example on the nitrogen—as the cation with at least one anion, which are physiologically acceptable—especially when used in humans and/or mammals. In particular, in the context of this invention by this there is understood the salt formed with a physiologically acceptable acid, namely salts of the particular active compound with inorganic or organic acids which are physiologically acceptable—especially when used in humans and/or mammals. Examples of physiologically acceptable salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, saccharic acid, monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, phosphoric acid, maleic acid, malonic acid, hippuric acid and/or aspartic acid. The hydrochloride salt, the citrate and the hemicitrate are particularly preferred.

In the context of this invention, the expression of salt formed with a physiologically acceptable acid is understood as meaning salts of the particular active compound with inorganic or organic acids which are physiologically acceptable—especially when used in humans and/or mammals. The hydrochloride and the citrate are particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, saccharic acid, monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, hippuric acid and/or aspartic acid.

In the context of this invention, the expression of physiologically acceptable salt with cations or bases is understood as meaning salts of at least one of the compounds according to the invention—usually of a (deprotonated) acid—as the anion with at least one preferably inorganic cation which are physiologically acceptable—especially when used in humans and/or mammals. The salts of the alkali metals and alkaline earth metals and also ammonium salts are particularly preferred, but especially (mono-) or (di-)sodium, (mono-) or (di-)potassium, magnesium or calcium salts.

In the context of this invention, the expression of salt formed with a physiologically acceptable cation is understood as meaning salts of at least one of the particular compounds as the anion with at least one inorganic cation which is physiologically acceptable—especially when used in humans and/or mammals. The salts of the alkali metals and alkaline earth metals and also ammonium salts are particularly preferred, but especially (mono-) or (di-)sodium, (mono-) or (di-)potassium, magnesium or calcium salts.

For a preferred embodiment of the substituted cyclohexyl-1,4-diamine derivatives according to the invention, $R^1$ and $R^2$ independently of one another represent H; $C_{1-5}$-alkyl, saturated or unsaturated, branched or unbranched, mono- or polysubstituted or unsubstituted;

or the radicals $R^1$ and $R^2$ together form a ring and denote $CH_2CH_2OCH_2CH_2$, $CH_2CH_2NR^{10}CH_2CH_2$ or $(CH_2)_{3-6}$, wherein $R^{10}$ denotes H; $C_{1-5}$-alkyl, saturated or unsaturated, branched or unbranched, mono- or polysubstituted or unsubstituted.

Particularly preferred substituted cyclohexyl-1,4-diamine derivatives are those wherein $R^1$ and $R^2$ independently of one another represent $CH_3$ or H, where $R^1$ and $R^2$ do not simultaneously denote H, or $R^1$ and $R^2$ represent $CH_2CH_2OCH_2CH_2$, $(CH_2)_4$, $(CH_2)_5$ or $(CH_2)_6$.

Substituted cyclohexyl-1,4-diamine derivatives which are furthermore preferred are those wherein $R^3$ represents cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl, in each case unsubstituted or mono- or polysubstituted; $C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bonded via a saturated, unbranched $C_{1-2}$-alkyl group and in each case unsubstituted or mono- or polysubstituted;

in particular $R^3$ denotes phenyl, furyl, thiophenyl, naphthyl, benzyl, benzofuranyl, indolyl, indanyl, benzodioxanyl, benzodioxolanyl, pyridyl, pyrimidyl, pyrazinyl or benzothiophenyl, in each case unsubstituted or mono- or polysubstituted; phenyl, furyl or thiophenyl bonded via a saturated, unbranched $C_{1-2}$-alkyl group and in each case unsubstituted or mono- or polysubstituted. Particularly preferred substituted cyclohexyl-1,4-diamine derivatives are those wherein $R^3$ represents phenyl, phenethyl, thiophenyl, pyridyl or benzyl, in each case substituted or unsubstituted, particularly preferably phenyl, thiophenyl, 4-chlorobenzyl, benzyl, 3-chlorobenzyl, 4-methylbenzyl, 2-chlorobenzyl, 4-fluorobenzyl, 3-methylbenzyl, 2-methylbenzyl, 3-fluorobenzyl, 2-fluorobenzyl or phenethyl.

Substituted cyclohexyl-1,4-diamine derivatives which are moreover preferred are those in which $R^4$ represents $C_{1-5}$-alkyl, cyclohexyl, cyclopentyl, cyclobutyl, cycloheptyl, cyclooctyl, phenyl, benzyl, naphthyl, anthracenyl, thiophenyl, benzothiophenyl, furanyl, isothiazolyl, imidazolyl, triazolyl, triazinyl, pyrazolyl, benzofuranyl, benzodioxolanyl, isoquinolinyl, phthalazinyl, benzo[1,2,5]thiadiazolyl, benzothiazolyl, benzotriazolyl, quinolinyl, carbazolyl, isoxazolyl, oxazolyl, indolyl, indanyl, benzodioxanyl, indazolyl, benzimidazolyl, pyrrolyl, pyridyl, pyrimidyl or pyrazinyl, in each case unsubstituted or mono- or polysubstituted; phenyl, naphthyl, anthracenyl, thiophenyl, benzothiophenyl. pyridyl, furyl, benzofuranyl, indolyl, indanyl, benzodioxanyl, pyrrolyl, pyrimidyl or pyrazinyl bonded via a saturated, unbranched substituted or unsubstituted $C_{1-2}$-alkyl group and in each case unsubstituted or mono- or polysubstituted, in particular $R^4$ represents $C_{1-5}$-alkyl, branched or unbranched, saturated or unsaturated, cyclohexyl, cyclopentyl, phenyl, benzyl, naphthyl, thiophenyl, benzothiophenyl, furanyl, pyrazolyl, benzofuranyl, isoquinolinyl, benzothiazolyl, benzotriazolyl, quinolinyl, isoxazolyl, oxazolyl, indolyl, pyrrolyl, pyridyl, pyrimidyl or pyrazinyl, in each case unsubstituted or mono- or polysubstituted, C(O)phenyl, benzyl or phenethyl, in each case unsubstituted or mono- or polysubstituted.

Substituted cyclohexyl-1,4-diamine derivatives which are particularly preferred are those in which $R^4$ represents phenyl, C(O)phenyl, $C_{1-5}$-alkyl, branched or unbranched, saturated or unsaturated, benzyl, pyridyl, pyrimidinyl or indolyl, in each case unsubstituted or mono- or polysubstituted.

Substituted cyclohexyl-1,4-diamine derivatives which are also preferred are those in which X represents $(CR^5R^6)_n$, phenyl, pyridyl, naphthyl, thiophenyl, furyl, pyrimidinyl or indolyl, in each case unsubstituted or mono- or polysubstituted and in each case also bridged via a $C_{1-3}$-alkyl chain, which can be substituted; where n=0, 1, 2, 3 or 4 and $R^5$, $R^6$ independently of one another represent H, $C_{1-5}$-alkyl, in each case saturated or unsaturated, branched or unbranched, mono- or polysubstituted or unsubstituted; phenyl, mono- or polysubstituted or unsubstituted.

Particularly preferred substituted cyclohexyl-1,4-diamine derivatives are those in which X represents vinylbenzyl, $C_{1-5}$-alkyl, branched or unbranched, saturated or unsaturated, phenethyl, phenyl, benzyl or pyridyl, in each case unsubstituted or mono- or polysubstituted.

Very particularly preferred substituted cyclohexyl-1,4-diamine derivatives are those from the group consisting of benzoic acid 2-[4-dimethylamino-4-(3-methyl-benzyl)-cyclohexylcarbamoyl]-benzyl ester 4-chloro-N-(2-{4-[1-(4-dimethylamino-4-phenyl-cyclohexylcarbamoyl)-1-methyl-ethoxy]-phenyl}-ethyl)-benzamide N-(4-dimethylamino-4-thiophen-2-yl-cyclohexyl)-2-(2-methoxy-ethoxy)-acetamide acetic acid (4-dimethylamino-4-thiophen-2-yl-cyclohexylcarbamoyl)-phenyl-methyl ester benzoic acid 2-[4-(3-chloro-benzyl)-4-dimethylamino-cyclohexylcarbamoyl]-benzyl ester acetic acid [4-dimethylamino-4-(3-fluoro-phenyl)-cyclohexylcarbamoyl]-phenyl-methyl ester N-[4-dimethylamino-4-(3-fluoro-phenyl)-cyclohexyl]-2-phenoxy-benzamide benzoic acid 2-[4-dimethylamino-4-(3-fluoro-phenyl)-cyclohexylcarbamoyl]-benzyl ester benzoic acid 2-[4-dimethylamino-4-(3-fluoro-phenyl)-cyclohexylcarbamoyl]-benzyl ester benzoic acid 2-(4-benzyl-4-dimethylamino-cyclohexylcarbamoyl)-benzyl ester benzoic acid 2-(4-dimethylamino-4-phenyl-cyclohexylcarbamoyl)-benzyl ester 2-(3-chloro-phenoxy)-N-(4-dimethylamino-4-phenyl-cyclohexyl)-acetamide N-[4-dimethylamino-4-(2-fluoro-benzyl)-cyclohexyl]-2-(4-methoxy-phenoxy)-5-nitro-benzamide benzoic acid 2-[4-dimethylamino-4-(2-fluoro-benzyl)-cyclohexylcarbamoyl]-benzyl ester benzoic acid 2-(4-dimethylamino-4-phenethyl-cyclohexylcarbamoyl)-benzyl ester benzoic acid 2-[4-dimethylamino-4-(4-methyl-benzyl)-cyclohexylcarbamoyl]-benzyl ester 2-benzylsulfanyl-N-(4-dimethylamino-4-thiophen-2-yl-cyclohexyl)-acetamide benzoic acid 2-[4-dimethylamino-4-(4-fluoro-benzyl)-cyclohexylcarbamoyl]-benzyl ester N-(4-dimethylamino-4-phenyl-cyclohexyl)-4-phenoxy-butyramide N-(4-dimethylamino-4-thiophen-2-yl-cyclohexyl)-2-phenoxy-acetamide benzoic acid 2-(4-benzyl-4-pyrrolidin-1-yl-cyclohexylcarbamoyl)-benzyl ester N-[4-dimethylamino-4-(3-methyl-benzyl)-cyclohexyl]-2-phenoxy-acetamide 4-[4-dimethylamino-4-(3-fluoro-phenyl)-cyclohexylcarbamoyl]-butyric acid methyl ester benzoic acid 2-[4-(4-chloro-benzyl)-4-dimethylamino-cyclohexylcarbamoyl]-benzyl ester N-(4-dimethylamino-4-phenyl-cyclohexyl)-2-(2-methoxy-ethoxy)-acetamide 5-(2,5-dimethyl-phenoxy)-2,2-dimethyl-pimelic acid [4-dimethylamino-4-(3-fluoro-phenyl)-cyclohexyl]-amide benzoic acid 2-[4-(2-chloro-benzyl)-4-dimethylamino-cyclohexylcarbamoyl]-benzyl ester 4-{1-[4-(2-chloro-benzyl)-4-dimethylamino-cyclohexylcarbamoyl]-1-methyl-ethoxy}-benzamide N-[4-(2-chloro-benzyl)-4-dimethylamino-cyclohexyl]-2-(2-chloro-phenoxy)-2-methyl-propionamide 2-(2-chloro-phenoxy)-N-[4-dimethylamino-4-(4-fluoro-benzyl)-cyclohexyl]-2-methyl-propionamide N-[4-dimethylamino-4-(3-fluoro-benzyl)-cyclohexyl]-2-(4-methoxy-phenoxy)-5-nitro-benzamide N-[4-(2-chloro-benzyl)-4-dimethylamino-cyclohexyl]-2-phenoxy-acetamide N-[4-dimethylamino-4-(3-methyl-benzyl)-cyclohexyl]-2-(4-methoxy-phenoxy)-5-nitro-benzamide N-[4-dimethylamino-4-(2-methyl-benzyl)-cyclohexyl]-2-phenoxy-benzamide 2-(4-chloro-phenoxy)-N-[4-dimethylamino-4-(2-fluoro-benzyl)-cyclohexyl]-acetamide N-[4-dimethylamino-4-(2-methyl-benzyl)-cyclohexyl]-2-phenoxy-acetamide N-[4-dimethylamino-4-(3-fluoro-benzyl)-cyclohexyl]-2-phenoxy-acetamide 2-(3-chloro-phenoxy)-N-[4-dimethylamino-4-phenethyl-cyclohexyl)-acetamide 2-(3-chloro-phenoxy)-N-[4-dimethylamino-4-(2-fluoro-benzyl)-cyclohexyl]-acetamide N-[4-(2-chloro-benzyl)-4-dimethylamino-cyclohexyl]-2-phenoxy-benzamide 2-(2-chloro-phenoxy)-N-[4-dimethylamino-4-(2-methyl-benzyl)-cyclohexyl]-2-methyl-propionamide N-[4-(2-chloro-benzyl)-4-dimethylamino-cyclohexyl]-2-phenoxy-propionamide 2-benzyloxy-N-[4-dimethylamino-4-(2-methyl-benzyl)-cyclohexyl]-acetamide acetic acid [4-dimethylamino-4-(3-fluoro-phenyl)-cyclohexylcarbamoyl]-methyl ester N-[4-dimethylamino-4-(2-fluoro-benzyl)-cyclohexyl]-2-phenoxy-butyramide
acetic acid [4-(2-chloro-benzyl)-4-dimethylamino-cyclohexylcarbamoyl]-phenyl-methyl ester
2-(4-chloro-phenoxy)-N-[4-dimethylamino-4-(2-methyl-benzyl)-cyclohexyl]-acetamide
2-(3-chloro-phenoxy)-N-[4-dimethylamino-4-(3-methyl-benzyl)-cyclohexyl]-acetamide
N-[4-dimethylamino-4-(4-fluoro-benzyl)-cyclohexyl]-2-phenoxy-benzamide
N-[4-dimethylamino-4-(2-methyl-benzyl)-cyclohexyl]-2-phenoxy-propionamide
2-benzyloxy-N-[4-(2-chloro-benzyl)-4-dimethylamino-cyclohexyl]-acetamide
N-[4-(3-chloro-benzyl)-4-dimethylamino-cyclohexyl]-2-(3-chloro-phenoxy)-acetamide
acetic acid (4-dimethylamino-4-thiophen-2-yl-cyclohexylcarbamoyl)-methyl ester
2-benzylsulfanyl-N-[4-dimethylamino-4-(4-methyl-benzyl)-cyclohexyl]-acetamide
N-[4-dimethylamino-4-(4-fluoro-benzyl)-cyclohexyl]-2-phenoxy-propionamide
N-[4-dimethylamino-4-(2-methyl-benzyl)-cyclohexyl]-4-phenoxy-butyramide
N-[4-(3-chloro-benzyl)-4-dimethylamino-cyclohexyl]-2-(4-methoxy-phenoxy)-5-nitro-benzamide
benzoic acid 2-(4-benzyl-4-piperidin-1-yl-cyclohexylcarbamoyl)-benzyl ester
N-[4-(2-chloro-benzyl)-4-dimethylamino-cyclohexyl]-2-phenoxy-butyramide
acetic acid [4-dimethylamino-4-(2-methyl-benzyl)-cyclohexylcarbamoyl]-phenyl-methyl ester
N-[4-dimethylamino-4-(2-fluoro-benzyl)-cyclohexyl]-2-phenoxy-acetamide
acetic acid (4-benzyl-4-piperidin-1-yl-cyclohexylcarbamoyl)-phenyl-methyl ester
N-[4-dimethylamino-4-(2-fluoro-benzyl)-cyclohexyl]-2-phenoxy-propionamide
2-benzylsulfanyl-N-[4-(3-chloro-benzyl)-4-dimethylamino-cyclohexyl]-acetamide
N-[4-dimethylamino-4-(3-fluoro-phenyl)-cyclohexyl]-2-methoxy-acetamide
N-[4-dimethylamino-4-(3-methyl-benzyl)-cyclohexyl]-2-phenylamino-benzamide
2-benzylsulfanyl-N-[4-dimethylamino-4-(3-methyl-benzyl)-cyclohexyl]-acetamide
N-(4-benzyl-4-dimethylamino-cyclohexyl)-2-(4-chloro-phenoxy)-acetamide
2-benzyloxy-N-[4-(3-chloro-benzyl)-4-dimethylamino-cyclohexyl]-acetamide
2-benzyloxy-N-[4-dimethylamino-4-(4-methyl-benzyl)-cyclohexyl]-acetamide
N-[4-(3-chloro-benzyl)-4-dimethylamino-cyclohexyl]-2-phenoxy-propionamide
N-[4-(3-chloro-benzyl)-4-dimethylamino-cyclohexyl]-2-phenoxy-acetamide
2-benzylsulfanyl-N-[4-(4-chloro-benzyl)-4-dimethylamino-cyclohexyl]-acetamide
4-{1-[4-dimethylamino-4-(4-fluoro-benzyl)-cyclohexylcarbamoyl]-1-methyl-ethoxy}-benzamide
N-[4-dimethylamino-4-(2-methyl-benzyl)-cyclohexyl]-2-phenoxy-butyramide
2-(4-chloro-phenoxy)-N-[4-dimethylamino-4-(3-fluoro-benzyl)-cyclohexyl]-acetamide
acetic acid (4-dimethylamino-4-phenethyl-cyclohexylcarbamoyl)-methyl ester
N-[4-dimethylamino-4-(4-fluoro-benzyl)-cyclohexyl]-4-phenoxy-butyramide
4-{1-[4-dimethylamino-4-(2-methyl-benzyl)-cyclohexylcarbamoyl]-1-methyl-ethoxy}-benzamide
benzoic acid 2-[2-(4-dimethylamino-4-phenethyl-cyclohexylcarbamoyl)-ethyl]-phenyl ester
acetic acid (4-benzyl-4-dimethylamino-cyclohexylcarbamoyl)-phenyl-methyl ester
N-[4-(2-chloro-benzyl)-4-dimethylamino-cyclohexyl]-2-(4-chloro-phenoxy)-acetamide
N-(4-benzyl-4-dimethylamino-cyclohexyl)-4-phenoxy-butyramide
N-[4-(4-chloro-benzyl)-4-dimethylamino-cyclohexyl]-2-(4-methoxy-phenoxy)-5-nitro-benzamide
2-(4-chloro-phenoxy)-N-[4-dimethylamino-4-(3-methyl-benzyl)-cyclohexyl]-acetamide
N-[4-(3-chloro-benzyl)-4-dimethylamino-cyclohexyl]-2-phenylamino-benzamide
acetic acid [4-dimethylamino-4-(3-methyl-benzyl)-cyclohexylcarbamoyl]-phenyl-methyl ester
acetic acid 1-[4-dimethylamino-4-(2-methyl-benzyl)-cyclohexylcarbamoyl]-ethyl ester
N-(4-benzyl-4-pyrrolidin-1-yl-cyclohexyl)-2-(4-chloro-phenoxy)-acetamide
N-(4-phenyl-4-piperidin-1-yl-cyclohexyl)-2-(5-trifluoromethyl-pyridin-2-ylsulfanyl)-acetamide
acetic acid [4-dimethylamino-4-(2-fluoro-benzyl)-cyclohexylcarbamoyl]-phenyl-methyl ester
2-(3-chloro-phenoxy)-N-[4-dimethylamino-4-(3-fluoro-benzyl)-cyclohexyl]-acetamide
N-(4-benzyl-4-dimethylamino-cyclohexyl)-2-phenoxy-propionamide
N-[4-dimethylamino-4-(2-fluoro-benzyl)-cyclohexyl]-2-(5-trifluoromethyl-pyridin-2-ylsulfanyl)-acetamide
4-(4-chloro-2-methyl-phenoxy)-N-(4-dimethylamino-4-phenethyl-cyclohexyl)-butyramide
acetic acid [4-dimethylamino-4-(3-fluoro-benzyl)-cyclohexylcarbamoyl]-phenyl-methyl ester
N-(4-dimethylamino-4-phenethyl-cyclohexyl)-4-phenoxy-butyramide
N-[4-dimethylamino-4-(3-fluoro-benzyl)-cyclohexyl]-2-phenoxy-propionamide
2-phenoxy-N-(4-phenyl-4-piperidin-1-yl-cyclohexyl)-butyramide
4-(4-chloro-2-methyl-phenoxy)-N-[4-dimethylamino-4-(3-methyl-benzyl)-cyclohexyl]-butyramide
N-[4-dimethylamino-4-(3-fluoro-benzyl)-cyclohexyl]-2-phenoxy-butyramide
N-[4-dimethylamino-4-(2-fluoro-benzyl)-cyclohexyl]-2-methylsulfanyl-acetamide
N-[4-(4-chloro-benzyl)-4-dimethylamino-cyclohexyl]-2-phenoxy-propionamide
2-(4-chloro-phenoxy)-N-[4-dimethylamino-4-(4-methyl-benzyl)-cyclohexyl]-acetamide
acetic acid [4-(3-chloro-benzyl)-4-dimethylamino-cyclohexylcarbamoyl]-phenyl-methyl ester
N-[4-dimethylamino-4-(3-fluoro-benzyl)-cyclohexyl]-2-methylsulfanyl-acetamide
acetic acid 1-(4-benzyl-4-dimethylamino-cyclohexylcarbamoyl)-ethyl ester
N-[4-dimethylamino-4-(4-fluoro-benzyl)-cyclohexyl]-2-phenoxy-butyramide
4-(4-chloro-2-methyl-phenoxy)-N-[4-dimethylamino-4-(4-methyl-benzyl)-cyclohexyl]-butyramide
N-[4-dimethylamino-4-(3-methyl-benzyl)-cyclohexyl]-2-(5-trifluoromethyl-pyridin-2-ylsulfanyl)-acetamide N-(4-dimethylamino-4-phenethyl-cyclohexyl)-2-phenoxy-propionamide
N-[4-dimethylamino-4-(2-fluoro-benzyl)-cyclohexyl]-2-ethoxy-acetamide
N-(4-benzyl-4-dimethylamino-cyclohexyl)-2-(5-trifluoromethyl-pyridin-2-ylsulfanyl)-acetamide
N-(4-benzyl-4-dimethylamino-cyclohexyl)-4-(chloro-2-methyl-phenoxy)-butyramide
2-benzyloxy-N-[4-(4-chloro-benzyl)-4-dimethylamino-cyclohexyl]-acetamide
benzoic acid 2-(4-azepan-1-yl-4-benzyl-cyclohexylcarbamoyl)-benzyl ester
N-[4-(3-chloro-benzyl)-4-dimethylamino-cyclohexyl]-2-(4-chloro-phenoxy)-acetamide
N-[4-dimethylamino-4-(4-fluoro-benzyl)-cyclohexyl]-2-phenoxy-acetamide
N-(4-benzyl-4-piperidin-1-yl-cyclohexyl)-2-(4-chloro-phenoxy)-acetamide
N-[4-dimethylamino-4-(4-methyl-benzyl)-cyclohexyl]-2-phenoxy-propionamide
4-(4-benzyl-4-dimethylamino-cyclohexylcarbamoyl)-butyric acid methyl ester
2-(4-chloro-phenoxy)-N-(4-dimethylamino-4-phenethyl-cyclohexyl)-acetamide
acetic acid [4-dimethylamino-4-(4-methyl-benzyl)-cyclohexylcarbamoyl]-phenyl-methyl ester
acetic acid [4-(2-chloro-benzyl)-4-dimethylamino-cyclohexylcarbamoyl]-methyl ester
4-chloro-N-[2-(4-{1-[4-dimethylamino-4-(3-fluoro-benzyl)-cyclohexylcarbamoyl]-1-methyl-ethoxy}-phenyl)-ethyl]-benzamide
4-chloro-N-[2-(4-{1-[4-dimethylamino-4-(2-fluoro-benzyl)-cyclohexylcarbamoyl]-1-methyl-ethoxy}-phenyl)-ethyl]-benzamide
N-[4-(4-chloro-benzyl)-4-dimethylamino-cyclohexyl]-4-phenoxy-butyramide
N-(4-benzyl-4-dimethylamino-cyclohexyl)-2-(2-methoxy-ethoxy)-acetamide
benzoic acid 2-{2-[4-dimethylamino-4-(3-methyl-benzyl)-cyclohexylcarbamoyl]-ethyl}-phenyl ester
benzoic acid 2-[2-(4-benzyl-4-piperidin-1-yl-cyclohexylcarbamoyl)-ethyl]-phenyl ester
N-[4-dimethylamino-4-(3-methyl-benzyl)-cyclohexyl]-2-phenoxy-nicotinamide
acetic acid [4-dimethylamino-4-(4-fluoro-benzyl)-cyclohexylcarbamoyl]-phenyl-methyl ester
N-(4-benzyl-4-piperidin-1-yl-cyclohexyl)-4-(4-chloro-2-methyl-phenoxy)-butyramide
N-(4-benzyl-4-pyrrolidin-1-yl-cyclohexyl)-2-phenoxy-propionamide
N-(4-benzyl-4-piperidin-1-yl-cyclohexyl)-2-phenoxy-acetamide
benzoic acid 2-(4-phenyl-4-piperidin-1-yl-cyclohexylcarbamoyl)-benzyl ester
4-[4-(3-chloro-benzyl)-4-dimethylamino-cyclohexylcarbamoyl]-butyric acid methyl ester
benzoic acid 2-[2-(4-phenyl-4-piperidin-1-yl-cyclohexylcarbamoyl)-ethyl]-phenyl ester
4-[4-dimethylamino-4-(4-fluoro-benzyl)-cyclohexylcarbamoyl]-butyric acid methyl ester
acetic acid 1-(4-benzyl-4-dimethylamino-cyclohexylcarbamoyl)-1-methyl-ethyl ester
acetic acid [4-(4-chloro-benzyl)-4-dimethylamino-cyclohexylcarbamoyl]-phenyl-methyl ester
benzoic acid 2-{2-[4-(3-chloro-benzyl)-4-dimethylamino-cyclohexylcarbamoyl]-ethyl}-phenyl ester
acetic acid 1-[4-dimethylamino-4-(3-fluoro-benzyl)-cyclohexylcarbamoyl]-1-methyl-ethyl ester
N-(4-azepan-1-yl-4-benzyl-cyclohexyl)-2-phenoxy-acetamide
4-chloro-N-(2-{4-[1-(4-dimethylamino-4-phenethyl-cyclohexylcarbamoyl)-1-methyl-ethoxy]-phenyl}-ethyl)-benzamide
N-[4-dimethylamino-4-(2-fluoro-benzyl)-cyclohexyl]-2-isopropylideneaminooxy-propionamide
N-[4-(3-chloro-benzyl)-4-dimethylamino-cyclohexyl]-succinic acid ethyl ester
N-[4-dimethylamino-4-(4-fluoro-benzyl)-cyclohexyl]-2-(pyrimidin-2-ylsulfanyl)-acetamide
acetic acid 1-[4-(4-chloro-benzyl)-4-dimethylamino-cyclohexylcarbamoyl]-1-methyl-ethyl ester
N-[4-(4-chloro-benzyl)-4-dimethylamino-cyclohexyl]-succinic acid ethyl ester
4-phenoxy-N-(4-phenyl-4-piperidin-1-yl-cyclohexyl)-butyramide
N-[4-(4-chloro-benzyl)-4-dimethylamino-cyclohexyl]-2-(4-chloro-phenoxy)-acetamide
acetic acid 1-(4-benzyl-4-piperidin-1-yl-cyclohexylcarbamoyl)-1-methyl-ethyl ester
5-[4-dimethylamino-4-(4-methyl-benzyl)-cyclohexylcarbamoyl]-pimelic acid methyl ester
N-[4-dimethylamino-4-(4-methyl-benzyl)-cyclohexyl]-3-methoxy-propionamide
acetic acid 1-[4-dimethylamino-4-(3-methyl-benzyl)-cyclohexylcarbamoyl]-1-methyl-ethyl ester
N-[4-(3-chloro-benzyl)-4-dimethylamino-cyclohexyl]-2-(2-methoxy-ethoxy)-acetamide
N-[4-dimethylamino-4-(3-methyl-benzyl)-cyclohexyl]-4-phenoxy-butyramide
5-[4-dimethylamino-4-(2-fluoro-benzyl)-cyclohexylcarbamoyl]-pimelic acid methyl ester
N-(4-benzyl-4-dimethylamino-cyclohexyl)-2-methylsulfanyl-acetamide
acetic acid 1-[4-dimethylamino-4-(4-methyl-benzyl)-cyclohexylcarbamoyl]-1-methyl-ethyl ester
N-(4-benzyl-4-piperidin-1-yl-cyclohexyl)-2-methoxy-acetamide
N-(4-morpholin-4-yl-4-phenyl-cyclohexyl)-succinic acid ethyl ester
5-(2,5-dimethyl-phenoxy)-2,2-dimethyl-pimelic acid (4-azepan-1-yl-4-benzyl-cyclohexyl)-amide
N-(4-azepan-1-yl-4-benzyl-cyclohexyl)-2-phenoxy-propionamide
N-[4-(4-chloro-benzyl)-4-dimethylamino-cyclohexyl]-2-methylsulfanyl-acetamide
N-[4-dimethylamino-4-(2-methyl-benzyl)-cyclohexyl]-2-methoxy-acetamide
4-(4-chloro-2-methyl-phenoxy)-N-(4-morpholin-4-yl-4-phenyl-cyclohexyl)-butyramide
N-[4-(3-chloro-benzyl)-4-dimethylamino-cyclohexyl]-2-methylsulfanyl-acetamide
N-[4-dimethylamino-4-(4-methyl-benzyl)-cyclohexyl]-2-(2-methoxy-ethoxy)-acetamide
N-(4-benzyl-4-piperidin-1-yl-cyclohexyl)-4-phenoxy-butyramide
acetic acid-1-[4-(2-chloro-benzyl)-4-dimethylamino-cyclohexylcarbamoyl]-1-methyl-ethyl ester
N-[4-(4-chloro-benzyl)-4-dimethylamino-cyclohexyl]-2-(2-methoxy-ethoxy)-acetamide
N-(2-{4-[1-(4-benzyl-4-piperidin-1-yl-cyclohexylcarbamoyl)-1-methyl-ethoxy]-phenyl}-ethyl)-4-chloro-benzamide acetic acid 1-(4-dimethylamino-4-phenethyl-cyclohexylcarbamoyl)-ethyl ester
N-[4-dimethylamino-4-(3-fluoro-benzyl)-cyclohexyl]-2-(2-methoxy-ethoxy)-acetamide
N-[4-(4-chloro-benzyl)-4-dimethylamino-cyclohexyl]-2-(5-trifluoromethyl-pyridin-2-ylsulfanyl)-acetamide
N-[4-dimethylamino-4-(4-methyl-benzyl)-cyclohexyl]-succinic acid methyl ester
3-(4-benzyloxy-3-methoxy-phenyl)-N-(4-phenyl-4-piperidin-1-yl-cyclohexyl)-acrylamide
N-[4-dimethylamino-4-(3-methyl-benzyl)-cyclohexyl]-2-(2-methoxy-ethoxy)-acetamide
4-[4-dimethylamino-4-(4-methyl-benzyl)-cyclohexylcarbamoyl]-butyric acid methyl ester
N-(4-benzyl-4-dimethylamino-cyclohexyl)-3-(4-benzyloxy-3-methoxy-phenyl)-acrylamide
N-(4-benzyl-4-dimethylamino-cyclohexyl)-2-methoxy-acetamide
acetic acid (4-morpholin-4-yl-4-phenyl-cyclohexylcarbamoyl)-methyl ester
4-(4-chloro-2-methyl-phenoxy)-N-[4-dimethylamino-4-(3-fluoro-benzyl)-cyclohexyl]-butyramide
N-(4-azepan-1-yl-4-benzyl-cyclohexyl)-2-(4-chloro-phenoxy)-acetamide
2-phenylamino-N-(4-phenyl-4-piperidin-1-yl-cyclohexyl)-benzamide
N-(2-{4-[1-(4-benzyl-4-pyrrolidin-1-yl-cyclohexylcarbamoyl)-1-methyl-ethoxy]-phenyl}-ethyl)-4-chloro-benzamide
4-chloro-N-[2-(4-{1-[4-(4-chloro-benzyl)-4-dimethylamino-cyclohexylcarbamoyl]-1-methyl-ethoxy}-phenyl)-ethyl]-benzamide
acetic acid [4-dimethylamino-4-(4-methyl-benzyl)-cyclohexylcarbamoyl]-methyl ester
acetic acid [4-dimethylamino-4-(3-fluoro-benzyl)-cyclohexylcarbamoyl]-methyl ester
acetic acid [4-(4-chloro-benzyl)-4-dimethylamino-cyclohexylcarbamoyl]-methyl ester
acetic acid [4-(3-chloro-benzyl)-4-dimethylamino-cyclohexylcarbamoyl]-methyl ester
4-[4-(4-chloro-benzyl)-4-dimethylamino-cyclohexylcarbamoyl]-butyric acid methyl ester
acetic acid 1-(4-morpholin-4-yl-4-phenyl-cyclohexylcarbamoyl)-ethyl ester
3-(4-benzyloxy-3-methoxy-phenyl)-N-[4-dimethylamino-4-(3-methyl-benzyl)-cyclohexyl]-acrylamide
3-(4-benzyloxy-3-methoxy-phenyl)-N-[4-dimethylamino-4-(4-methyl-benzyl)-cyclohexyl]-acrylamide
acetic acid [4-dimethylamino-4-(3-methyl-benzyl)-cyclohexylcarbamoyl]-methyl ester
3-(4-benzyloxy-3-methoxy-phenyl)-N-[4-(3-chloro-benzyl)-4-dimethylamino-cyclohexyl]-acrylamide
N-(4-morpholin-4-yl-4-phenyl-cyclohexyl)-2-phenylamino-benzamide
N-[4-(4-chloro-benzyl)-4-dimethylamino-cyclohexyl]-2-isopropylideneaminooxy-propionamide
4-chloro-N-(2-{4-[1-methyl-1-(4-phenyl-4-piperidin-1-yl-cyclohexylcarbamoyl)-ethoxy]-phenyl}-ethyl)-benzamide
N-[4-(3-chloro-benzyl)-4-dimethylamino-cyclohexyl]-2-isopropylideneaminooxy-propionamide
N-(4-morpholin-4-yl-4-phenyl-cyclohexyl)-2-(5-trifluoromethyl-pyridin-2-ylsulfanyl)-acetamide
N-(4-phenyl-4-piperidin-1-yl-cyclohexyl)-succinic acid methyl ester
benzoic acid 2-(4-morpholin-4-yl-4-phenyl-cyclohexylcarbamoyl)-benzyl ester
N-[4-(3-chloro-benzyl)-4-dimethylamino-cyclohexyl]-succinic acid methyl ester
4-chloro-N-(2-{4-[1-methyl-1-(4-morpholin-4-yl-4-phenyl-cyclohexylcarbamoyl)-ethoxy]-phenyl}-ethyl)-benzamide
5-[4-(2-chloro-benzyl)-4-dimethylamino-cyclohexylcarbamoyl]-pimelic acid methyl ester
4-(4-phenyl-4-piperidin-1-yl-cyclohexylcarbamoyl)-butyric acid methyl ester
acetic acid 1-[4-dimethylamino-4-(3-methyl-benzyl)-cyclohexylcarbamoyl]-ethyl ester
N-[4-dimethylamino-4-(3-methyl-benzyl)-cyclohexyl]-succinic acid methyl ester
4-chloro-N-[2-(4-{1-[4-dimethylamino-4-(3-methyl-benzyl)-cyclohexylcarbamoyl]-1-methyl-ethoxy}-phenyl)-ethyl]-benzamide
N-[4-dimethylamino-4-(2-fluoro-benzyl)-cyclohexyl]-succinic acid methyl ester
acetic acid 1-[4-(3-chloro-benzyl)-4-dimethylamino-cyclohexylcarbamoyl]-ethyl ester
acetic acid 1-[4-(4-chloro-benzyl)-4-dimethylamino-cyclohexylcarbamoyl]-ethyl ester
N-(4-benzyl-4-piperidin-1-yl-cyclohexyl)-2-phenylamino-benzamide
acetic acid 1-(4-benzyl-4-piperidin-1-yl-cyclohexylcarbamoyl)-ethyl ester
4-chloro-N-[2-(4-{1-[4-(3-chloro-benzyl)-4-dimethylamino-cyclohexylcarbamoyl]-1-methyl-ethoxy}-phenyl)-ethyl]-benzamide
4-chloro-N-[2-(4-{1-[4-dimethylamino-4-(4-methyl-benzyl)-cyclohexylcarbamoyl]-1-methyl-ethoxy}-phenyl)-ethyl]-benzamide
acetic acid 1-[4-dimethylamino-4-(4-methyl-benzyl)-cyclohexylcarbamoyl]-ethyl ester
4-[4-dimethylamino-4-(3-fluoro-benzyl)-cyclohexylcarbamoyl]-butyric acid methyl ester
4-[4-dimethylamino-4-(3-methyl-benzyl)-cyclohexylcarbamoyl]-butyric acid methyl ester
N-(4-morpholin-4-yl-4-phenyl-cyclohexyl)-succinic acid methyl ester
acetic acid 1-[4-dimethylamino-4-(2-fluoro-benzyl)-cyclohexylcarbamoyl]-ethyl ester
4-[4-dimethylamino-4-(2-fluoro-benzyl)-cyclohexylcarbamoyl]-butyric acid methyl ester
3-(4-benzyloxy-3-methoxy-phenyl)-N-[4-dimethylamino-4-(3-fluoro-benzyl)-cyclohexyl]-acrylamide
benzoic acid 2-{2-[4-(4-chloro-benzyl)-4-dimethylamino-cyclohexylcarbamoyl]-ethyl}-phenyl ester
4-(4-morpholin-4-yl-4-phenyl-cyclohexylcarbamoyl)-butyric acid methyl ester
acetic acid 1-[4-dimethylamino-4-(3-fluoro-benzyl)-cyclohexylcarbamoyl]-ethyl ester
3-(4-benzyloxy-3-methoxy-phenyl)-N-(4-dimethylamino-4-phenethyl-cyclohexyl)-acrylamide
N-[4-(2-chloro-benzyl)-4-dimethylamino-cyclohexyl]-2-ethoxy-acetamide
3-(4-benzyloxy-3-methoxy-phenyl)-N-[4-(4-chloro-benzyl)-4-dimethylamino-cyclohexyl]-acrylamide
3-(4-benzyloxy-3-methoxy-phenyl)-N-[4-dimethylamino-4-(2-fluoro-benzyl)-cyclohexyl]-acrylamide
2-(3-chlorophenoxy)-N-(4-dimethylamino-4-phenylcyclohexyl)acetamide hydrochloride, more polar diastereoisomer
2-(3-chlorophenoxy)-N-(4-dimethylamino-4-phenylcyclohexyl)acetamide hydrochloride, less polar diastereoisomer
N-(4-dimethylamino-4-phenylcyclohexyl)-4-phenoxybutyramide hydrochloride, more polar diastereoisomer N-(4-dimethylamino-4-phenylcyclohexyl)-4-phenoxybutyramide hydrochloride, less polar diastereoisomer in the form of the racemate; the enantiomers, diastereomers, mixtures of the enantiomers or diastereomers or an individual enantiomer or diastereomer; the bases and/or salts of physiologically acceptable acids or cations.

The substances according to the invention have an action, for example, on the μ-opioid receptor, which is relevant in connection with various diseases, so that they are suitable as a pharmaceutical active compound in a medicament. The invention therefore also provides medicaments comprising at least one substituted cyclohexyl-1,4-diamine derivative according to the invention and optionally suitable additives and/or auxiliary substances and/or optionally further active compounds.

In addition to at least one substituted cyclohexyl-1,4-diamine derivative according to the invention, the medicaments according to the invention optionally comprise suitable additives and/or auxiliary substances, thus also carrier materials, fillers, solvents, diluents, dyestuffs and/or binders, and can be administered as liquid medicament forms in the form of injection solutions, drops or juices, as semi-solid medicament forms in the form of granules, tablets, pellets, patches, capsules, plasters/spray plasters or aerosols. The choice of the auxiliary substances etc. and the amounts thereof to be employed depend on whether the medicament is to be administered orally, perorally, parenterally, intravenously, intraperitoneally, intradermally, intramuscularly, intranasally, buccally, rectally or locally, for example to the skin, the mucous membranes or into the eyes. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Substituted cyclohexyl-1,4-diamine derivatives according to the invention in a depot, in dissolved form or in a plaster, optionally with the addition of agents which promote penetration through the skin, are suitable formulations for percutaneous administration. Formulation forms which can be used orally or percutaneously can release the substituted cyclohexyl-1,4-diamine derivatives according to the invention in a delayed manner. The substituted cyclohexyl-1,4-diamine derivatives according to the invention can also be used in parenteral long-term depot forms, such as e.g. implants or implanted pumps. Other further active compounds known to the expert can in principle be added to the medicaments according to the invention.

The amount of active compound to be administered to the patient varies according to the weight of the patient, the mode of administration, the indication and the severity of the disease. 0.00005 to 50 mg/kg, preferably 0.01 to 5 mg/kg of at least one substituted cyclohexyl-1,4-diamine derivative according to the invention are conventionally administered.

For all the above forms of the medicaments according to the invention, it is particularly preferable if the medicament also comprises, in addition to at least one substituted cyclohexyl-1,4-diamine derivative, a further active compound, in particular an opioid, preferably a potent opioid, in particular morphine, or an anaesthetic, preferably hexobarbital or halothane.

In a preferred form of the medicament, a substituted cyclohexyl-1,4-diamine derivative according to the invention contained therein is in the form of a pure diastereomer and/or enantiomer, a racemate or a non-equimolar or equimolar mixture of the diastereomers and/or enantiomers.

The ORL1 receptor, and also the other opioid receptors, have been identified in particular in the pain event. Substituted cyclohexyl-1,4-diamine derivatives according to the invention can accordingly be used for the preparation of a medicament for treatment of pain, in particular acute, neuropathic or chronic pain.

The invention therefore also provides the use of a substituted cyclohexyl-1,4-diamine derivative according to the invention for the preparation of a medicament for treatment of pain, in particular acute, visceral, neuropathic or chronic pain.

The invention also provides the use of a substituted cyclohexyl-1,4-diamine derivative according to the invention for the preparation of a medicament for treatment of anxiety states, of stress and stress-associated syndromes, depressions, epilepsy, Alzheimer's disease, senile dementia, catalepsy, general cognitive dysfunctions, learning and memory disorders (as a nootropic), withdrawal symptoms, alcohol and/or drug and/or medicament abuse and/or dependency, sexual dysfunctions, cardiovascular diseases, hypotension, hypertension, tinnitus, pruritus, migraine, impaired hearing, deficient intestinal motility, impaired food intake, anorexia, obesity, locomotor disorders, diarrhea, cachexia, urinary incontinence and as a muscle relaxant, anticonvulsive or anaesthetic and for co-administration with treatment with an opioid analgesic or with an anaesthetic, for diuresis or antinatriuresis, anxiolysis, for modulation of movement activity, for modulation of neurotransmitter secretion and treatment of neurodegenerative diseases associated therewith, for treatment of withdrawal symptoms and/or for reducing the addiction potential of opioids.

In this context, in one of the above uses it may be preferable for a substituted cyclohexyl-1,4-diamine derivative used to be in the form of a pure diastereomer and/or enantiomer, a racemate or a non-equimolar or equimolar mixture of the diastereomers and/or enantiomers.

The invention also provides a method for treatment, in particular in one of the abovementioned indications, of a non-human mammal or human which or who requires treatment of pain, in particular chronic pain, by administration of a therapeutically active dose of a substituted cyclohexyl-1,4-diamine derivative according to the invention or of a medicament according to the invention.

The invention also provides a process for the preparation of the substituted cyclohexyl-1,4-diamine derivatives according to the invention as described in the following description and examples.

The radicals $R^{01}$ and $R^{02}$ have the meaning given for $R^1$ and $R^2$ for compounds according to formula I according to the invention, and can additionally independently of one another represent a protective group. The other radicals have the meaning given in formula I:

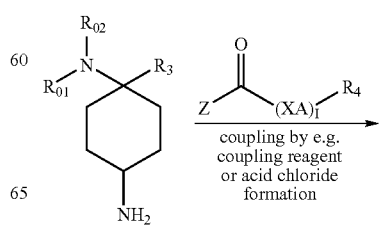

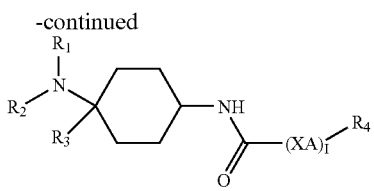

Z = OH, Cl, active ester

The diverse methods known to the expert for the preparation of amides are in principle suitable for the preparation of the substances according to the invention.

The process according to the invention is preferably based on linking substituted cyclohexane-1,4-diamines (WO 02090317) with suitable carboxylic acids and/or carboxylic acid derivatives, in particular carboxylic acid chlorides or bromides, and converting them into compounds according to the invention in this way.

Polar or nonpolar aprotic solvents to which an organic or inorganic auxiliary base, preferably tertiary amines, such as triethylamine, diusopropylethylamine or DMAP, has been added are employed in reactions with acid chlorides and bromides. In addition to such amines, pyridine, for example, is also suitable as a base and as a solvent. Preferably, acid chlorides are reacted with amines at −30 to +40° C. in methylene chloride or chloroform in the presence of triethylamine or pyridine and optionally catalytic amounts of DMAP. The entire range of methods known to the expert for the preparation of amides is also available for the reaction of carboxylic acids with a substituted cyclohexane-1,4-diamine (WO 02090317). The use of organic or inorganic dehydrating agents, such as e.g. a molecular sieve, magnesium sulfate, sulfuric acid or carboduimides, such as DCC or DIC, the latter optionally in the presence of HOBt, is advantageous in this context. These reactions are also preferably carried out in polar or nonpolar aprotic solvents at temperatures of between −30 and +110° C., preferably −10 and +40° C. If appropriate, the protective groups are then split off.

EXAMPLES

The following examples serve to explain the invention in more detail, but do not limit the general inventive idea.

The yields of the compounds prepared are not optimized. All the temperatures are uncorrected.

The term "ether" denotes diethyl ether, "EA" denotes ethyl acetate and "MC" denotes methylene chloride. The term "equivalent" means equivalent substance amount, "m.p." denotes melting point or melting range, "decomp." denotes decomposition, "RT" denotes room temperature, "abs." denotes absolute (anhydrous), "rac." denotes racemic, "conc." denotes concentrated, "min" denotes minutes, "h" denotes hours, "d" denotes days, "vol. %" denotes per cent by volume, "wt. %" denotes per cent by weight and "M" is the concentration stated in mol/l.

Silica gel 60 (0.040-0.063 mm) from E. Merck, Darmstadt was employed as the stationary phase for the column chromatography.

The thin layer chromatography analyses were carried out with HPTLC precoated plates, silica gel 60 F 254 from E. Merck, Darmstadt.

The mixture ratios of mobile phases for chromatographic analyses are always stated in volume/volume.

The compounds employed in the following either were commercially obtainable or their preparation is known from the prior art or has been deduced from the prior art in a manner obvious to the expert.

General Instructions:

0.1 mmol of an acid chloride which has been prepared from the corresponding carboxylic acids by methods known to the expert (see Table 1) was added to 0.1 mmol of the cyclohexane-1,4-diamine in the presence of 1.05 equivalents of triethylamine. The mixture was stirred for 12 h and a 1 M sodium carbonate solution was then added. The product was obtained by extraction with in each case 3×2 ml methylene chloride and removal of the solvent.

The carboxylic acids employed for the last step for the examples are named in Table 1.

TABLE 1

Names of the example compounds and structures of the carboxylic acids employed in the last step

| Compound | Acid employed | Name |
|---|---|---|
| Example 1 | | benzoic acid 2-[4-dimethylamino-4-(3-methyl-benzyl)-cyclohexylcarbamoyl]-benzyl ester |
| Example 2 | | 4-chloro-N-(2-{4-[1-(4-dimethylamino-4-phenyl-cyclohexylcarbamoyl)-1-methyl-ethoxy]-phenyl}-ethyl)-benzamide |
| Example 3 | | N-(4-dimethylamino-4-thiophen-2-yl-cyclohexyl)-2-(2-methoxy-ethoxy)-acetamide |

TABLE 1-continued

Names of the example compounds and structures of the
carboxylic acids employed in the last step

| Compound | Acid employed | Name |
| --- | --- | --- |
| Example 4 | | acetic acid (4-dimethylamino-4-thiophen-2-yl-cyclohexylcarbamoyl)-phenyl-methyl ester |
| Example 5 | | benzoic acid 2-[4-(3-chloro-benzyl)-4-dimethylamino-cyclohexylcarbamoyl]-benzyl ester |
| Example 6 | | acetic acid [4-dimethylamino-4-(3-fluoro-phenyl)-cyclohexylcarbamoyl]-phenyl-methyl ester |
| Example 7 | | N-[4-dimethylamino-4-(3-fluoro-phenyl)-cyclohexyl]-2-phenoxy-benzamide |
| Example 8 | | benzoic acid 2-[4-dimethylamino-4-(3-fluoro-phenyl)-cyclohexylcarbamoyl]-benzyl ester |
| Example 9 | | benzoic acid 2-[4-dimethylamino-4-(3-fluoro-benzyl)-cyclohexylcarbamoyl]-benzyl ester |
| Example 10 | | benzoic acid 2-(4-benzyl-4-dimethylamino-cyclohexylcarbamoyl)-benzyl ester |

TABLE 1-continued

Names of the example compounds and structures of the carboxylic acids employed in the last step

| Compound | Acid employed | Name |
|---|---|---|
| Example 11 | | benzoic acid 2-(4-dimethylamino-4-phenyl-cyclohexylcarbamoyl)-benzyl ester |
| Example 12 | | 2-(3-chloro-phenoxy)-N-(4-dimethylamino-4-phenyl-cyclohexyl)-acetamide |
| Example 13 | | N-[4-dimethylamino-4-(2-fluoro-benzyl)-cyclohexyl]-2-(4-methoxy-phenoxy)-5-nitro-benzamide |
| Example 14 | | benzoic acid 2-[4-dimethylamino-4-(2-fluoro-benzyl)-cyclohexylcarbamoyl]-benzyl ester |
| Example 15 | | benzoic acid 2-(4-dimethylamino-4-phenethyl-cyclohexylcarbamoyl)-benzyl ester |
| Example 16 | | benzoic acid 2-[4-dimethylamino-4-(4-methyl-benzyl)-cyclohexylcarbamoyl]-benzyl ester |
| Example 17 | | 2-benzylsulfanyl-N-(4-dimethylamino-4-thiophen-2-yl-cyclohexyl)-acetamide |
| Example 18 | | benzoic acid 2-[4-dimethylamino-4-(4-fluoro-benzyl)-cyclohexylcarbamoyl]-benzyl ester |

TABLE 1-continued

Names of the example compounds and structures of the carboxylic acids employed in the last step

| Compound | Acid employed | Name |
|---|---|---|
| Example 19 | 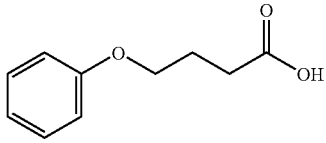 | N-(4-dimethylamino-4-phenyl-cyclohexyl)-4-phenoxy-butyramide |
| Example 20 | 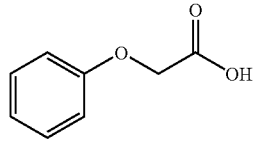 | N-(4-dimethylamino-4-thiophen-2-yl-cyclohexyl)-2-phenoxy-acetamide |
| Example 21 | 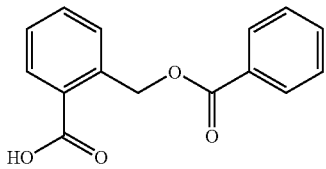 | benzoic acid 2-(4-benzyl-4-pyrrolidin-1-yl-cyclohexylcarbamoyl)-benzyl ester |
| Example 22 | 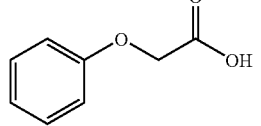 | N-[4-dimethylamino-4-(3-methyl-benzyl)-cyclohexyl]-2-phenoxy-acetamide |
| Example 23 | 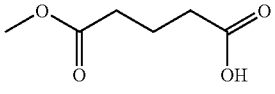 | 4-[4-dimethylamino-4-(3-fluoro-phenyl)-cyclohexylcarbamoyl]-butyric acid methyl ester |
| Example 24 | 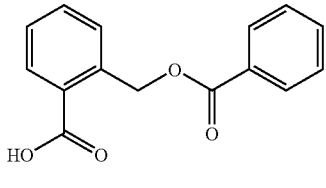 | benzoic acid 2-[4-(4-chloro-benzyl)-4-dimethylamino-cyclohexylcarbamoyl]-benzyl ester |
| Example 25 | 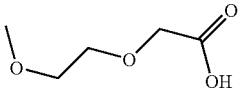 | N-(4-dimethylamino-4-phenyl-cyclohexyl)-2-(2-methoxy-ethoxy)-acetamide |
| Example 26 | 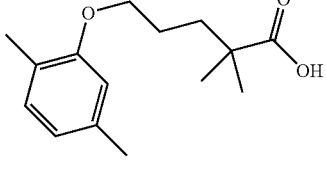 | 5-(2,5-dimethyl-phenoxy)-2,2-dimethyl-pimelic acid [4-dimethylamino-4-(3-fluoro-phenyl)-cyclohexyl]-amide |
| Example 27 | 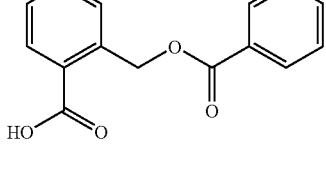 | benzoic acid 2-[4-(2-chloro-benzyl)-4-dimethylamino-cyclohexylcarbamoyl]-benzyl ester |

TABLE 1-continued

Names of the example compounds and structures of the
carboxylic acids employed in the last step

| Compound | Acid employed | Name |
| --- | --- | --- |
| Example 28 | | 4-{1-[4-(2-chloro-benzyl)-4-dimethylamino-cyclohexylcarbamoyl]-1-methyl-ethoxy}-benzamide |
| Example 29 | | N-[4-(2-chloro-benzyl)-4-dimethylamino-cyclohexyl]-2-(2-chloro-phenoxy)-2-methyl-propionamide |
| Example 30 | | 2-(2-chloro-phenoxy)-N-[4-dimethylamino-4-(4-fluoro-benzyl)-cyclohexyl]-2-methyl-propionamide |
| Example 31 | | N-[4-dimethylamino-4-(3-fluoro-benzyl)-cyclohexyl]-2-(4-methoxy-phenoxy)-5-nitro-benzamide |
| Example 32 | | N-[4-(2-chloro-benzyl)-4-dimethylamino-cyclohexyl]-2-phenoxy-acetamide |
| Example 33 | | N-[4-dimethylamino-4-(3-methyl-benzyl)-cyclohexyl]-2-(4-methoxy-phenoxy)-5-nitro-benzamide |
| Example 34 | | N-[4-dimethylamino-4-(2-methyl-benzyl)-cyclohexyl]-2-phenoxy-benzamide |

TABLE 1-continued

Names of the example compounds and structures of the
carboxylic acids employed in the last step

| Compound | Acid employed | Name |
| --- | --- | --- |
| Example 35 | (4-chlorophenoxyacetic acid) | 2-(4-chloro-phenoxy)-N-[4-dimethylamino-4-(2-fluoro-benzyl)-cyclohexyl]-acetamide |
| Example 36 | (phenoxyacetic acid) | N-[4-dimethylamino-4-(2-methyl-benzyl)-cyclohexyl]-2-phenoxy-acetamide |
| Example 37 | (phenoxyacetic acid) | N-[4-dimethylamino-4-(3-fluoro-benzyl)-cyclohexyl]-2-phenoxy-acetamide |
| Example 38 | (3-chlorophenoxyacetic acid) | 2-(3-chloro-phenoxy)-N-(4-dimethylamino-4-phenethyl-cyclohexyl)-acetamide |
| Example 39 | (3-chlorophenoxyacetic acid) | 2-(3-chloro-phenoxy)-N-[4-dimethylamino-4-(2-fluoro-benzyl)-cyclohexyl]-acetamide |
| Example 40 | (2-phenoxybenzoic acid) | N-[4-(2-chloro-benzyl)-4-dimethylamino-cyclohexyl]-2-phenoxy-benzamide |
| Example 41 | (2-(2-chlorophenoxy)-2-methylpropionic acid) | 2-(2-chloro-phenoxy)-N-[4-dimethylamino-4-(2-methyl-benzyl)-cyclohexyl]-2-methyl-propionamide |
| Example 42 | (2-phenoxypropionic acid) | N-[4-(2-chloro-benzyl)-4-dimethylamino-cyclohexyl]-2-phenoxy-propionamide |

TABLE 1-continued

Names of the example compounds and structures of the carboxylic acids employed in the last step

| Compound | Acid employed | Name |
| --- | --- | --- |
| Example 43 | | 2-benzyloxy-N-[4-dimethylamino-4-(2-methyl-benzyl)-cyclohexyl]-acetamide |
| Example 44 | | acetic acid [4-dimethylamino-4-(3-fluoro-phenyl)-cyclohexylcarbamoyl]-methyl ester |
| Example 45 | | N-[4-dimethylamino-4-(2-fluoro-benzyl)-cyclohexyl]-2-phenoxy-butyramide |
| Example 46 | | acetic acid [4-(2-chloro-benzyl)-4-dimethylamino-cyclohexylcarbamoyl]-phenyl-methyl ester |
| Example 47 | | 2-(4-chloro-phenoxy)-N-[4-dimethylamino-4-(2-methyl-benzyl)-cyclohexyl]-acetamide |
| Example 48 | | 2-(3-chloro-phenoxy)-N-[4-dimethylamino-4-(3-methyl-benzyl)-cyclohexyl]-acetamide |
| Example 49 | | N-[4-dimethylamino-4-(4-fluoro-benzyl)-cyclohexyl]-2-phenoxy-benzamide |
| Example 50 | | N-[4-dimethylamino-4-(2-methyl-benzyl)-cyclohexyl]-2-phenoxy-propionamide |
| Example 51 | | 2-benzyloxy-N-[4-(2-chloro-benzyl)-4-dimethylamino-cyclohexyl]-acetamide |

TABLE 1-continued

Names of the example compounds and structures of the carboxylic acids employed in the last step

| Compound | Acid employed | Name |
| --- | --- | --- |
| Example 52 | | N-[4-(3-chloro-benzyl)-4-dimethylamino-cyclohexyl]-2-(3-chloro-phenoxy)-acetamide |
| Example 53 | | acetic acid (4-dimethylamino-4-thiophen-2-yl-cyclohexylcarbamoyl)-methyl ester |
| Example 54 | | 2-benzylsulfanyl-N-[4-dimethylamino-4-(4-methyl-benzyl)-cyclohexyl]-acetamide |
| Example 55 | | N-[4-dimethylamino-4-(4-fluoro-benzyl)-cyclohexyl]-2-phenoxy-propionamide |
| Example 56 | | N-[4-dimethylamino-4-(2-methyl-benzyl)-cyclohexyl]-4-phenoxy-butyramide |
| Example 57 | | N-[4-(3-chloro-benzyl)-4-dimethylamino-cyclohexyl]-2-(4-methoxy-phenoxy)-5-nitro-benzamide |
| Example 58 | | benzoic acid 2-(4-benzyl-4-piperidin-1-yl-cyclohexylcarbamoyl)-benzyl ester |
| Example 59 | | N-[4-(2-chloro-benzyl)-4-dimethylamino-cyclohexyl]-2-phenoxy-butyramide |

TABLE 1-continued

Names of the example compounds and structures of the carboxylic acids employed in the last step

| Compound | Acid employed | Name |
| --- | --- | --- |
| Example 60 | | acetic acid [4-dimethylamino-4-(2-methyl-benzyl)-cyclohexylcarbamoyl]-phenyl-methyl ester |
| Example 61 | | N-[4-dimethylamino-4-(2-fluoro-benzyl)-cyclohexyl]-2-phenoxy-acetamide |
| Example 62 | | acetic acid (4-benzyl-4-piperidin-1-yl-cyclohexylcarbamoyl)-phenyl-methyl ester |
| Example 63 | | N-[4-dimethylamino-4-(2-fluoro-benzyl)-cyclohexyl]-2-phenoxy-propionamide |
| Example 64 | | 2-benzylsulfanyl-N-[4-(3-chloro-benzyl)-4-dimethylamino-cyclohexyl]-acetamide |
| Example 65 | | N-[4-dimethylamino-4-(3-fluoro-phenyl)-cyclohexyl]-2-methoxy-acetamide |
| Example 66 | | N-[4-dimethylamino-4-(3-methyl-benzyl)-cyclohexyl]-2-phenylamino-benzamide |
| Example 67 | | 2-benzylsulfanyl-N-[4-dimethylamino-4-(3-methyl-benzyl)-cyclohexyl]-acetamide |

TABLE 1-continued

Names of the example compounds and structures of the carboxylic acids employed in the last step

| Compound | Acid employed | Name |
| --- | --- | --- |
| Example 68 | | N-(4-benzyl-4-dimethylamino-cyclohexyl)-2-(4-chloro-phenoxy)-acetamide |
| Example 69 | | 2-benzyloxy-N-[4-(3-chloro-benzyl)-4-dimethylamino-cyclohexyl]-acetamide |
| Example 70 | | 2-benzyloxy-N-[4-dimethylamino-4-(4-methyl-benzyl)-cyclohexyl]-acetamide |
| Example 71 | | N-[4-(3-chloro-benzyl)-4-dimethylamino-cyclohexyl]-2-phenoxy-propionamide |
| Example 72 | | N-[4-(3-chloro-benzyl)-4-dimethylamino-cyclohexyl]-2-phenoxy-acetamide |
| Example 73 | | 2-benzylsulfanyl-N-[4-(4-chloro-benzyl)-4-dimethylamino-cyclohexyl]-acetamide |
| Example 74 | | 4-{1-[4-dimethylamino-4-(4-fluoro-benzyl)-cyclohexylcarbamoyl]-1-methyl-ethoxy}-benzamide |
| Example 75 | | N-[4-dimethylamino-4-(2-methyl-benzyl)-cyclohexyl]-2-phenoxy-butyramide |
| Example 76 | | 2-(4-chloro-phenoxy)-N-[4-dimethylamino-4-(3-fluoro-benzyl)-cyclohexyl]-acetamide |
| Example 77 | | acetic acid (4-dimethylamino-4-phenethyl-cyclohexylcarbamoyl)-methyl ester |

TABLE 1-continued

Names of the example compounds and structures of the
carboxylic acids employed in the last step

| Compound | Acid employed | Name |
| --- | --- | --- |
| Example 78 | | N-[4-dimethylamino-4-(4-fluoro-benzyl)-cyclohexyl]-4-phenoxy-butyramide |
| Example 79 | | 4-{1-[4-dimethylamino-4-(2-methyl-benzyl)-cyclohexylcarbamoyl]-1-methyl-ethoxy}-benzamide |
| Example 80 | | benzoic acid 2-[2-(4-dimethylamino-4-phenethyl-cyclohexylcarbamoyl)-ethyl]-phenyl ester |
| Example 81 | | acetic acid (4-benzyl-4-dimethylamino-cyclohexylcarbamoyl)-phenyl-methyl ester |
| Example 82 | | N-[4-(2-chloro-benzyl)-4-dimethylamino-cyclohexyl]-2-(4-chloro-phenoxy)-acetamide |
| Example 83 | | N-(4-benzyl-4-dimethylamino-cyclohexyl)-4-phenoxy-butyramide |
| Example 84 | | N-[4-(4-chloro-benzyl)-4-dimethylamino-cyclohexyl]-2-(4-methoxy-phenoxy)-5-nitro-benzamide |
| Example 85 | | 2-(4-chloro-phenoxy)-N-[4-dimethylamino-4-(3-methyl-benzyl)-cyclohexyl]-acetamide |

TABLE 1-continued

Names of the example compounds and structures of the carboxylic acids employed in the last step

| Compound | Acid employed | Name |
| --- | --- | --- |
| Example 86 | | N-[4-(3-chloro-benzyl)-4-dimethylamino-cyclohexyl]-2-phenylamino-benzamide |
| Example 87 | | acetic acid [4-dimethylamino-4-(3-methyl-benzyl)-cyclohexylcarbamoyl]-phenyl-methyl ester |
| Example 88 | | acetic acid 1-[4-dimethylamino-4-(2-methyl-benzyl)-cyclohexylcarbamoyl]-ethyl ester |
| Example 89 | | N-(4-benzyl-4-pyrrolidin-1-yl-cyclohexyl)-2-(4-chloro-phenoxy)-acetamide |
| Example 90 | | N-(4-phenyl-4-piperidin-1-yl-cyclohexyl)-2-(5-trifluoromethyl-pyridin-2-ylsulfanyl)-acetamide |
| Example 91 | | acetic acid [4-dimethylamino-4-(2-fluoro-benzyl)-cyclohexylcarbamoyl]-phenyl-methyl ester |
| Example 92 | | 2-(3-chloro-phenoxy)-N-[4-dimethylamino-4-(3-fluoro-benzyl)-cyclohexyl]-acetamide |

TABLE 1-continued

Names of the example compounds and structures of the carboxylic acids employed in the last step

| Compound | Acid employed | Name |
| --- | --- | --- |
| Example 93 | | N-(4-benzyl-4-dimethylamino-cyclohexyl)-2-phenoxy-propionamide |
| Example 94 | | N-[4-dimethylamino-4-(2-fluoro-benzyl)-cyclohexyl]-2-(5-trifluoromethyl-pyridin-2-ylsulfanyl)-acetamide |
| Example 95 | | 4-(4-chloro-2-methyl-phenoxy)-N-(4-dimethylamino-4-phenethyl-cyclohexyl)-butyramide |
| Example 96 | | acetic acid [4-dimethylamino-4-(3-fluoro-benzyl)-cyclohexylcarbamoyl]-phenyl-methyl ester |
| Example 97 | | N-(4-dimethylamino-4-phenethyl-cyclohexyl)-4-phenoxy-butyramide |
| Example 98 | | N-[4-dimethylamino-4-(3-fluoro-benzyl)-cyclohexyl]-2-phenoxy-propionamide |
| Example 99 | | 2-phenoxy-N-(4-phenyl-4-piperidin-1-yl-cyclohexyl)-butyramide |
| Example 100 | | 4-(4-chloro-2-methyl-phenoxy)-N-[4-dimethylamino-4-(3-methyl-benzyl)-cyclohexyl]-butyramide |
| Example 101 | | N-[4-dimethylamino-4-(3-fluoro-benzyl)-cyclohexyl]-2-phenoxy-butyramide |

TABLE 1-continued

Names of the example compounds and structures of the carboxylic acids employed in the last step

| Compound | Acid employed | Name |
| --- | --- | --- |
| Example 102 | (structure) | N-[4-dimethylamino-4-(2-fluoro-benzyl)-cyclohexyl]-2-methylsulfanyl-acetamide |
| Example 103 | (structure) | N-[4-(4-chloro-benzyl)-4-dimethylamino-cyclohexyl]-2-phenoxy-propionamide |
| Example 104 | (structure) | 2-(4-chloro-phenoxy)-N-[4-dimethylamino-4-(4-methyl-benzyl)-cyclohexyl]-acetamide |
| Example 105 | (structure) | acetic acid [4-(3-chloro-benzyl)-4-dimethylamino-cyclohexylcarbamoyl]-phenyl-methyl ester |
| Example 106 | (structure) | N-[4-dimethylamino-4-(3-fluoro-benzyl)-cyclohexyl]-2-methylsulfanyl-acetamide |
| Example 107 | (structure) | acetic acid 1-(4-benzyl-4-dimethylamino-cyclohexylcarbamoyl)-ethyl ester |
| Example 108 | (structure) | N-[4-dimethylamino-4-(4-fluoro-benzyl)-cyclohexyl]-2-phenoxy-butyramide |
| Example 109 | (structure) | 4-(4-chloro-2-methyl-phenoxy)-N-[4-dimethylamino-4-(4-methyl-benzyl)-cyclohexyl]-butyramide |
| Example 110 | (structure) | N-[4-dimethylamino-4-(3-methyl-benzyl)-cyclohexyl]-2-(5-trifluoromethyl-pyridin-2-ylsulfanyl)-acetamide |

TABLE 1-continued

Names of the example compounds and structures of the
carboxylic acids employed in the last step

| Compound | Acid employed | Name |
| --- | --- | --- |
| Example 111 | (structure: 2-phenoxypropanoic acid) | N-(4-dimethylamino-4-phenethyl-cyclohexyl)-2-phenoxy-propionamide |
| Example 112 | (structure: 3-methoxypropanoic acid) | N-[4-dimethylamino-4-(2-fluoro-benzyl)-cyclohexyl]-2-ethoxy-acetamide |
| Example 113 | (structure: (5-trifluoromethyl-pyridin-2-ylsulfanyl)-acetic acid) | N-(4-benzyl-4-dimethylamino-cyclohexyl)-2-(5-trifluoromethyl-pyridin-2-ylsulfanyl)-acetamide |
| Example 114 | (structure: 4-(4-chloro-2-methyl-phenoxy)-butyric acid) | N-(4-benzyl-4-dimethylamino-cyclohexyl)-4-(4-chloro-2-methyl-phenoxy)-butyramide |
| Example 115 | (structure: benzyloxy-acetic acid) | 2-benzyloxy-N-[4-(4-chloro-benzyl)-4-dimethylamino-cyclohexyl]-acetamide |
| Example 116 | (structure: 2-(benzoyloxymethyl)benzoic acid) | benzoic acid 2-(4-azepan-1-yl-4-benzyl-cyclohexylcarbamoyl)-benzyl ester |
| Example 117 | (structure: (4-chloro-phenoxy)-acetic acid) | N-[4-(3-chloro-benzyl)-4-dimethylamino-cyclohexyl]-2-(4-chloro-phenoxy)-acetamide |
| Example 118 | (structure: phenoxy-acetic acid) | N-[4-dimethylamino-4-(4-fluoro-benzyl)-cyclohexyl]-2-phenoxy-acetamide |
| Example 119 | (structure: (4-chloro-phenoxy)-acetic acid) | N-(4-benzyl-4-piperidin-1-yl-cyclohexyl)-2-(4-chloro-phenoxy)-acetamide |

TABLE 1-continued

Names of the example compounds and structures of the carboxylic acids employed in the last step

| Compound | Acid employed | Name |
| --- | --- | --- |
| Example 120 | | N-[4-dimethylamino-4-(4-methyl-benzyl)-cyclohexyl]-2-phenoxy-propionamide |
| Example 121 | | 4-(4-benzyl-4-dimethylamino-cyclohexylcarbamoyl)-butyric acid methyl ester |
| Example 122 | | 2-(4-chloro-phenoxy)-N-(4-dimethylamino-4-phenethyl-cyclohexyl)-acetamide |
| Example 123 | | acetic acid [4-dimethylamino-4-(4-methyl-benzyl)-cyclohexylcarbamoyl]-phenyl-methyl ester |
| Example 124 | | acetic acid [4-(2-chloro-benzyl)-4-dimethylamino-cyclohexylcarbamoyl]-methyl ester |
| Example 125 | | 4-chloro-N-[2-(4-{1-[4-dimethylamino-4-(3-fluoro-benzyl)-cyclohexylcarbamoyl]-1-methyl-ethoxy}-phenyl)-ethyl]-benzamide |
| Example 126 | | 4-chloro-N-[2-(4-{1-[4-dimethylamino-4-(2-fluoro-benzyl)-cyclohexylcarbamoyl]-1-methyl-ethoxy}-phenyl)-ethyl]-benzamide |
| Example 127 | | N-[4-(4-chloro-benzyl)-4-dimethylamino-cyclohexyl]-4-phenoxy-butyramide |
| Example 128 | | N-(4-benzyl-4-dimethylamino-cyclohexyl)-2-(2-methoxy-ethoxy)-acetamide |

TABLE 1-continued

Names of the example compounds and structures of the
carboxylic acids employed in the last step

| Compound | Acid employed | Name |
|---|---|---|
| Example 129 | 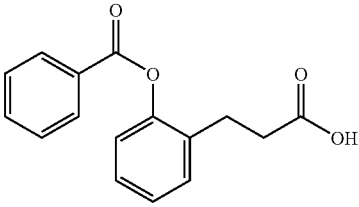 | benzoic acid 2-{2-[4-dimethylamino-4-(3-methyl-benzyl)-cyclohexylcarbamoyl]-ethyl}-phenyl ester |
| Example 130 | 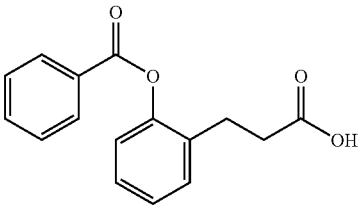 | benzoic acid 2-[2-(4-benzyl-4-piperidin-1-yl-cyclohexylcarbamoyl)-ethyl]-phenyl ester |
| Example 131 | 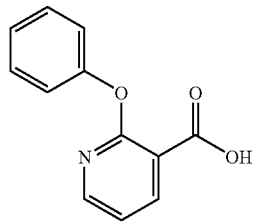 | N-[4-dimethylamino-4-(3-methyl-benzyl)-cyclohexyl]-2-phenoxy-nicotinamide |
| Example 132 | 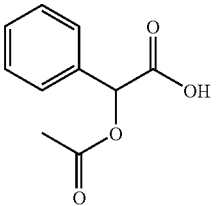 | acetic acid [4-dimethylamino-4-(4-fluoro-benzyl)-cyclohexylcarbamoyl]-phenyl-methyl ester |
| Example 133 | 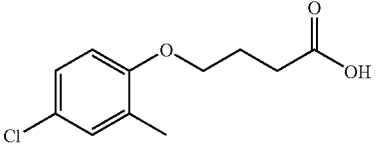 | N-(4-benzyl-4-piperidin-1-yl-cyclohexyl)-4-(4-chloro-2-methyl-phenoxy)-butyramide |
| Example 134 | 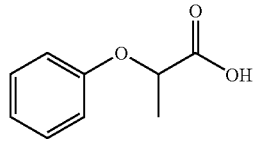 | N-(4-benzyl-4-pyrrolidin-1-yl-cyclohexyl)-2-phenoxy-propionamide |
| Example 135 | 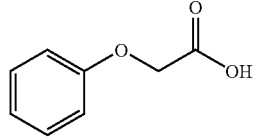 | N-(4-benzyl-4-piperidin-1-yl-cyclohexyl)-2-phenoxy-acetamide |

TABLE 1-continued

Names of the example compounds and structures of the carboxylic acids employed in the last step

| Compound | Acid employed | Name |
|---|---|---|
| Example 136 | | benzoic acid 2-(4-phenyl-4-piperidin-1-yl-cyclohexylcarbamoyl)-benzyl ester |
| Example 137 | | 4-[4-(3-chloro-benzyl)-4-dimethylamino-cyclohexylcarbamoyl]-butyric acid methyl ester |
| Example 138 | | benzoic acid 2-[2-(4-phenyl-4-piperidin-1-yl-cyclohexylcarbamoyl)-ethyl]-phenyl ester |
| Example 139 | | 4-[4-dimethylamino-4-(4-fluoro-benzyl)-cyclohexylcarbamoyl]-butyric acid methyl ester |
| Example 140 | | acetic acid 1-(4-benzyl-4-dimethylamino-cyclohexylcarbamoyl)-1-methyl-ethyl ester |
| Example 141 | | acetic acid [4-(4-chloro-benzyl)-4-dimethylamino-cyclohexylcarbamoyl]-phenyl-methyl ester |
| Example 142 | | benzoic acid 2-{2-[4-(3-chloro-benzyl)-4-dimethylamino-cyclohexylcarbamoyl]-ethyl}-phenyl ester |
| Example 143 | | acetic acid 1-[4-dimethylamino-4-(3-fluoro-benzyl)-cyclohexylcarbamoyl]-1-methyl-ethyl ester |
| Example 144 | | N-(4-azepan-1-yl-4-benzyl-cyclohexyl)-2-phenoxy-acetamide |

TABLE 1-continued

Names of the example compounds and structures of the carboxylic acids employed in the last step

| Compound | Acid employed | Name |
|---|---|---|
| Example 145 | | 4-chloro-N-(2-{4-[1-(4-dimethylamino-4-phenethyl-cyclohexylcarbamoyl)-1-methyl-ethoxy]-phenyl}-ethyl)-benzamide |
| Example 146 | | N-[4-dimethylamino-4-(2-fluoro-benzyl)-cyclohexyl]-2-isopropylideneaminooxy-propionamide |
| Example 147 | | N-[4-(3-chloro-benzyl)-4-dimethylamino-cyclohexyl]-succinic acid ethyl ester |
| Example 148 | | N-[4-dimethylamino-4-(4-fluoro-benzyl)-cyclohexyl]-2-(pyrimidin-2-ylsulfanyl)-acetamide |
| Example 149 | | acetic acid 1-[4-(4-chloro-benzyl)-4-dimethylamino-cyclohexylcarbamoyl]-1-methyl-ethyl ester |
| Example 150 | | N-[4-(4-chloro-benzyl)-4-dimethylamino-cyclohexyl]-succinic acid ethyl ester |
| Example 151 | | 4-phenoxy-N-(4-phenyl-4-piperidin-1-yl-cyclohexyl)-butyramide |
| Example 152 | | N-[4-(4-chloro-benzyl)-4-dimethylamino-cyclohexyl]-2-(4-chloro-phenoxy)-acetamide |
| Example 153 | | acetic acid 1-(4-benzyl-4-piperidin-1-yl-cyclohexylcarbamoyl)-1-methyl-ethyl ester |
| Example 154 | | 5-[4-dimethylamino-4-(4-methyl-benzyl)-cyclohexylcarbamoyl]-pimelic acid methyl ester |

TABLE 1-continued

Names of the example compounds and structures of the carboxylic acids employed in the last step

| Compound | Acid employed | Name |
| --- | --- | --- |
| Example 155 | | N-[4-dimethylamino-4-(4-methyl-benzyl)-cyclohexyl]-3-methoxy-propionamide |
| Example 156 | | acetic acid 1-[4-dimethylamino-4-(3-methyl-benzyl)-cyclohexylcarbamoyl]-1-methyl-ethyl ester |
| Example 157 | | N-[4-(3-chloro-benzyl)-4-dimethylamino-cyclohexyl]-2-(2-methoxy-ethoxy)-acetamide |
| Example 158 | | N-[4-dimethylamino-4-(3-methyl-benzyl)-cyclohexyl]-4-phenoxy-butyramide |
| Example 159 | | 5-[4-dimethylamino-4-(2-fluoro-benzyl)-cyclohexylcarbamoyl]-pimelic acid methyl ester |
| Example 160 | | N-(4-benzyl-4-dimethylamino-cyclohexyl)-2-methylsulfanyl-acetamide |
| Example 161 | | acetic acid 1-[4-dimethylamino-4-(4-methyl-benzyl)-cyclohexylcarbamoyl]-1-methyl-ethyl ester |
| Example 162 | | N-(4-benzyl-4-piperidin-1-yl-cyclohexyl)-2-methoxy-acetamide |
| Example 163 | | N-(4-morpholin-4-yl-4-phenyl-cyclohexyl)-succinic acid ethyl ester |
| Example 164 | | 5-(2,5-dimethyl-phenoxy)-2,2-dimethyl-pimelic acid (4-azepan-1-yl-4-benzyl-cyclohexyl)-amide |
| Example 165 | | N-(4-azepan-1-yl-4-benzyl-cyclohexyl)-2-phenoxy-propionamide |

TABLE 1-continued

Names of the example compounds and structures of the carboxylic acids employed in the last step

| Compound | Acid employed | Name |
| --- | --- | --- |
| Example 166 | methylsulfanyl-acetic acid | N-[4-(4-chloro-benzyl)-4-dimethylamino-cyclohexyl]-2-methylsulfanyl-acetamide |
| Example 167 | methoxy-acetic acid | N-[4-dimethylamino-4-(2-methyl-benzyl)-cyclohexyl]-2-methoxy-acetamide |
| Example 168 | 4-(4-chloro-2-methyl-phenoxy)-butyric acid | 4-(4-chloro-2-methyl-phenoxy)-N-(4-morpholin-4-yl-4-phenyl-cyclohexyl)-butyramide |
| Example 169 | methylsulfanyl-acetic acid | N-[4-(3-chloro-benzyl)-4-dimethylamino-cyclohexyl]-2-methylsulfanyl-acetamide |
| Example 170 | (2-methoxy-ethoxy)-acetic acid | N-[4-dimethylamino-4-(4-methyl-benzyl)-cyclohexyl]-2-(2-methoxy-ethoxy)-acetamide |
| Example 171 | 4-phenoxy-butyric acid | N-(4-benzyl-4-piperidin-1-yl-cyclohexyl)-4-phenoxy-butyramide |
| Example 172 | 2-acetoxy-2-methyl-propanoic acid | acetic acid-1-[4-(2-chloro-benzyl)-4-dimethylamino-cyclohexylcarbamoyl]-1-methyl-ethyl ester |
| Example 173 | (2-methoxy-ethoxy)-acetic acid | N-[4-(4-chloro-benzyl)-4-dimethylamino-cyclohexyl]-2-(2-methoxy-ethoxy)-acetamide |
| Example 174 | | N-(2-{4-[1-(4-benzyl-4-piperidin-1-yl-cyclohexylcarbamoyl)-1-methyl-ethoxyl-phenyl}-ethyl)-4-chloro-benzamide |
| Example 175 | 2-acetoxy-propanoic acid | acetic acid 1-(4-dimethylamino-4-phenethyl-cyclohexylcarbamoyl)-ethyl ester |
| Example 176 | (2-methoxy-ethoxy)-acetic acid | N-[4-dimethylamino-4-(3-fluoro-benzyl)-cyclohexyl]-2-(2-methoxy-ethoxy)-acetamide |

TABLE 1-continued

Names of the example compounds and structures of the carboxylic acids employed in the last step

| Compound | Acid employed | Name |
| --- | --- | --- |
| Example 177 | | N-[4-(4-chloro-benzyl)-4-dimethylamino-cyclohexyl]-2-(5-trifluoromethyl-pyridin-2-ylsulfanyl)-acetamide |
| Example 178 | | N-[4-dimethylamino-4-(4-methyl-benzyl)-cyclohexyl]-succinic acid methyl ester |
| Example 179 | | 3-(4-benzyloxy-3-methoxy-phenyl)-N-(4-phenyl-4-piperidin-1-yl-cyclohexyl)-acrylamide |
| Example 180 | | N-[4-dimethylamino-4-(3-methyl-benzyl)-cyclohexyl]-2-(2-methoxy-ethoxy)-acetamide |
| Example 181 | | 4-[4-dimethylamino-4-(4-methyl-benzyl)-cyclohexylcarbamoyl]-butyric acid methyl ester |
| Example 182 | | N-(4-benzyl-4-dimethylamino-cyclohexyl)-3-(4-benzyloxy-3-methoxy-phenyl)-acrylamide |
| Example 183 | | N-(4-benzyl-4-dimethylamino-cyclohexyl)-2-methoxy-acetamide |
| Example 184 | | acetic acid (4-morpholin-4-yl-4-phenyl-cyclohexylcarbamoyl)-methyl ester |
| Example 185 | | 4-(4-chloro-2-methyl-phenoxy)-N-[4-dimethylamino-4-(3-fluoro-benzyl)-cyclohexyl]-butyramide |

TABLE 1-continued

Names of the example compounds and structures of the carboxylic acids employed in the last step

| Compound | Acid employed | Name |
| --- | --- | --- |
| Example 186 | | N-(4-azepan-1-yl-4-benzyl-cyclohexyl)-2-(4-chloro-phenoxy)-acetamide |
| Example 187 | | 2-phenylamino-N-(4-phenyl-4-piperidin-1-yl-cyclohexyl)-benzamide |
| Example 188 | | N-(2-{4-[1-(4-benzyl-4-pyrrolidin-1-yl-cyclohexylcarbamoyl)-1-methyl-ethoxy]-phenyl}-ethyl)-4-chloro-benzamide |
| Example 189 | | 4-chloro-N-[2-(4-{1-[4-(4-chloro-benzyl)-4-dimethylamino-cyclohexylcarbamoyl]-1-methyl-ethoxy}-phenyl)-ethyl]-benzamide |
| Example 190 | | acetic acid [4-dimethylamino-4-(4-methyl-benzyl)-cyclohexylcarbamoyl]-methyl ester |
| Example 191 | | acetic acid [4-dimethylamino-4-(3-fluoro-benzyl)-cyclohexylcarbamoyl]-methyl ester |
| Example 192 | | acetic acid [4-(4-chloro-benzyl)-4-dimethylamino-cyclohexylcarbamoyl]-methyl ester |
| Example 193 | | acetic acid [4-(3-chloro-benzyl)-4-dimethylamino-cyclohexylcarbamoyl]-methyl ester |
| Example 194 | | 4-[4-(4-chloro-benzyl)-4-dimethylamino-cyclohexylcarbamoyl]-butyric acid methyl ester |

TABLE 1-continued

Names of the example compounds and structures of the carboxylic acids employed in the last step

| Compound | Acid employed | Name |
| --- | --- | --- |
| Example 195 | | acetic acid 1-(4-morpholin-4-yl-4-phenyl-cyclohexylcarbamoyl)-ethyl ester |
| Example 196 | | 3-(4-benzyloxy-3-methoxy-phenyl)-N-[4-dimethylamino-4-(3-methyl-benzyl)-cyclohexyl]-acrylamide |
| Example 197 | | 3-(4-benzyloxy-3-methoxy-phenyl)-N-[4-dimethylamino-4-(4-methyl-benzyl)-cyclohexyl]-acrylamide |
| Example 198 | | acetic acid [4-dimethylamino-4-(3-methyl-benzyl)-cyclohexylcarbamoyl]-methyl ester |
| Example 199 | | 3-(4-benzyloxy-3-methoxy-phenyl)-N-[4-(3-chloro-benzyl)-4-dimethylamino-cyclohexyl]-acrylamide |
| Example 200 | | N-(4-morpholin-4-yl-4-phenyl-cyclohexyl)-2-phenylamino-benzamide |
| Example 201 | | N-[4-(4-chloro-benzyl)-4-dimethylamino-cyclohexyl]-2-isopropylideneaminooxy-propionamide |
| Example 202 | | 4-chloro-N-(2-{4-[1-methyl-1-(4-phenyl-4-piperidin-1-yl-cyclohexylcarbamoyl)-ethoxy]-phenyl}-ethyl)-benzamide |

TABLE 1-continued

Names of the example compounds and structures of the
carboxylic acids employed in the last step

| Compound | Acid employed | Name |
|---|---|---|
| Example 203 | (structure) | N-[4-(3-chloro-benzyl)-4-dimethylamino-cyclohexyl]-2-isopropylideneaminooxy-propionamide |
| Example 204 | (structure) | N-(4-morpholin-4-yl-4-phenyl-cyclohexyl)-2-(5-trifluoromethyl-pyridin-2-ylsulfanyl)-acetamide |
| Example 205 | (structure) | N-(4-phenyl-4-piperidin-1-yl-cyclohexyl)-succinic acid methyl ester |
| Example 206 | (structure) | benzoic acid 2-(4-morpholin-4-yl-4-phenyl-cyclohexylcarbamoyl)-benzyl ester |
| Example 207 | (structure) | N-[4-(3-chloro-benzyl)-4-dimethylamino-cyclohexyl]-succinic acid methyl ester |
| Example 208 | (structure) | 4-chloro-N-(2-{4-[1-methyl-1-(4-morpholin-4-yl-4-phenyl-cyclohexylcarbamoyl)-ethoxy]-phenyl}-ethyl)-benzamide |
| Example 209 | (structure) | 5-[4-(2-chloro-benzyl)-4-dimethylamino-cyclohexylcarbamoyl]-pimelic acid methyl ester |
| Example 210 | (structure) | 4-(4-phenyl-4-piperidin-1-yl-cyclohexylcarbamoyl)-butyric acid methyl ester |
| Example 211 | (structure) | acetic acid 1-[4-dimethylamino-4-(3-methyl-benzyl)-cyclohexylcarbamoyl]-ethyl ester |
| Example 212 | (structure) | N-[4-dimethylamino-4-(3-methyl-benzyl)-cyclohexyl]-succinic acid methyl ester |

TABLE 1-continued

Names of the example compounds and structures of the
carboxylic acids employed in the last step

| Compound | Acid employed | Name |
|---|---|---|
| Example 213 | 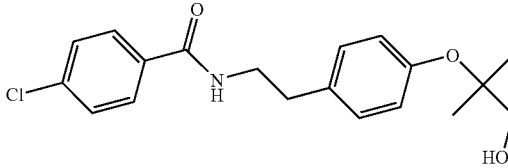 | 4-chloro-N-[2-(4-{1-[4-dimethylamino-4-(3-methyl-benzyl)-cyclohexylcarbamoyl]-1-methyl-ethoxy}-phenyl)-ethyl]-benzamide |
| Example 214 | 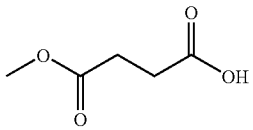 | N-[4-dimethylamino-4-(2-fluoro-benzyl)-cyclohexyl]-succinic acid methyl ester |
| Example 215 | 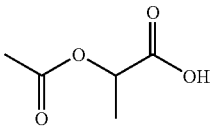 | acetic acid 1-[4-(3-chloro-benzyl)-4-dimethylamino-cyclohexylcarbamoyl]-ethyl ester |
| Example 216 | 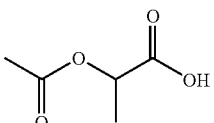 | acetic acid 1-[4-(4-chloro-benzyl)-4-dimethylamino-cyclohexylcarbamoyl]-ethyl ester |
| Example 217 | 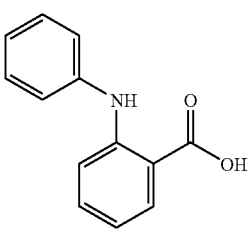 | N-(4-benzyl-4-piperidin-1-yl-cyclohexyl)-2-phenylamino-benzamide |
| Example 218 | 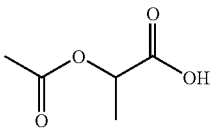 | acetic acid 1-(4-benzyl-4-piperidin-1-yl-cyclohexylcarbamoyl)-ethyl ester |
| Example 219 | 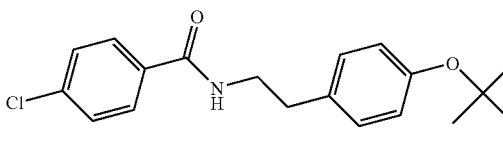 | 4-chloro-N-[2-(4-{1-[4-(3-chloro-benzyl)-4-dimethylamino-cyclohexylcarbamoyl]-1-methyl-ethoxy}-phenyl)-ethyl]-benzamide |
| Example 220 | 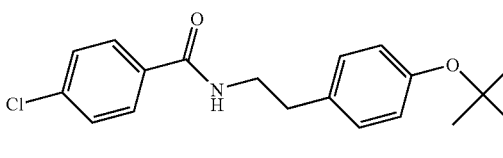 | 4-chloro-N-[2-(4-{1-[4-dimethylamino-4-(4-methyl-benzyl)-cyclohexylcarbamoyl]-1-methyl-ethoxy}-phenyl)-ethyl]-benzamide |
| Example 221 | 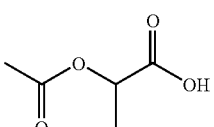 | acetic acid 1-[4-dimethylamino-4-(4-methyl-benzyl)-cyclohexylcarbamoyl]-ethyl ester |

TABLE 1-continued

Names of the example compounds and structures of the carboxylic acids employed in the last step

| Compound | Acid employed | Name |
| --- | --- | --- |
| Example 222 | | 4-[4-dimethylamino-4-(3-fluoro-benzyl)-cyclohexylcarbamoyl]-butyric acid methyl ester |
| Example 223 | | 4-[4-dimethylamino-4-(3-methyl-benzyl)-cyclohexylcarbamoyl]-butyric acid methyl ester |
| Example 224 | | N-(4-morpholin-4-yl-4-phenyl-cyclohexyl)-succinic acid methyl ester |
| Example 225 | | acetic acid 1-[4-dimethylamino-4-(2-fluoro-benzyl)-cyclohexylcarbamoyl]-ethyl ester |
| Example 226 | | 4-[4-dimethylamino-4-(2-fluoro-benzyl)-cyclohexylcarbamoyl]-butyric acid methyl ester |
| Example 227 | | 3-(4-benzyloxy-3-methoxy-phenyl)-N-[4-dimethylamino-4-(3-fluoro-benzyl)-cyclohexyl]-acrylamide |
| Example 228 | | benzoic acid 2-{2-[4-(4-chloro-benzyl)-4-dimethylamino-cyclohexylcarbamoyl]-ethyl}-phenyl ester |
| Example 229 | | 4-(4-morpholin-4-yl-4-phenyl-cyclohexylcarbamoyl)-butyric acid methyl ester |
| Example 230 | | acetic acid 1-[4-dimethylamino-4-(3-fluoro-benzyl)-cyclohexylcarbamoyl]-ethyl ester |
| Example 231 | | 3-(4-benzyloxy-3-methoxy-phenyl)-N-(4-dimethylamino-4-phenethyl-cyclohexyl)-acrylamide |

TABLE 1-continued

Names of the example compounds and structures of the
carboxylic acids employed in the last step

| Compound | Acid employed | Name |
| --- | --- | --- |
| Example 232 | methoxy-propanoic acid structure | N-[4-(2-chloro-benzyl)-4-dimethylamino-cyclohexyl]-2-ethoxy-acetamide |
| Example 233 | 3-(4-benzyloxy-3-methoxyphenyl)acrylic acid (propanoic acid form) structure | 3-(4-benzyloxy-3-methoxy-phenyl)-N-[4-(4-chloro-benzyl)-4-dimethylamino-cyclohexyl]-acrylamide |
| Example 234 | 3-(4-benzyloxy-3-methoxyphenyl)propanoic acid structure | 3-(4-benzyloxy-3-methoxy-phenyl)-N-[4-dimethylamino-4-(2-fluoro-benzyl)-cyclohexyl]-acrylamide |

Some example compounds were synthesized on a larger scale.

Example 235

2-(3-Chlorophenoxy)-N-(4-dimethylamino-4-phenylcyclohexyl)acetamide hydrochloride, More Polar Diastereoisomer A cis/trans mixture of N,N-dimethyl-1-phenylcyclohexane-1,4-diamine (800 mg) was initially introduced into the reaction vessel with 540 µl triethylamine (1.05 molar equivalents) and catalytic amounts of DMAP (approx. 15 mg) in 20 ml methylene chloride, 790 mg (3-chlorophenoxy)acetyl chloride (1.05 molar equivalents) were added dropwise at −20° C. and the mixture was stirred overnight, while warming to room temperature. For working up, the mixture was rendered alkaline (pH>10) with one molar sodium hydroxide solution and extracted with diethyl ether (3×20 ml), the combined extracts were dried over sodium sulfate and filtered and the filtrate was concentrated to dryness. The crude product obtained (1.53 g) was chromatographed on silica gel (3.0×17 cm) with 100 ml diethyl ether followed by 500 ml diethyl ether/methanol (v:v=2:1). 346 mg of the more polar diastereoisomer of 2-(3-chlorophenoxy)-N-(4-dimethylamino-4-phenylcyclohexyl)acetamide were obtained and, as a solution in 5 ml 2-butanone and 5 ml ethyl acetate, were converted into the corresponding hydrochloride by addition of 16 µl water and 110 µl chlorotrimethylsilane (322 mg of a white solid, m.p. 220° C.).

Example 236

2-(3-Chlorophenoxy)-N-(4-dimethylamino-4-phenylcyclohexyl)acetamide hydrochloride, Less Polar Diastereoisomer As described for Example 235, 356 mg of the less polar diastereoisomer of 2-(3-chlorophenoxy)-N-(4-dimethylamino-4-phenylcyclohexyl)acetamide were also obtained and, as a solution in 5 ml 2-butanone and 10 ml ethyl acetate, were converted into the corresponding hydrochloride by addition of 17 µl water and 117 µl chlorotrimethylsilane (338 mg of a white solid, m.p. 223-224.5° C.).

Example 237

N-(4-Dimethylamino-4-phenylcyclohexyl)-4-phenoxybutyramide hydrochloride, More Polar Diastereoisomer As described for Example 235, a cis/trans mixture of N,N-dimethyl-1-phenylcyclohexane-1,4-diamine (800 mg) was reacted with 0.95 mg 4-phenoxybutyryl chloride and the crude product (1.48 g) was isolated analogously. By chromatography on silica gel (3.0×19 cm) with 100 ml diethyl ether followed by 400 ml diethyl ether/methanol (v:v=2:1), 450 mg of the more polar diastereoisomer of N-(4-dimethylamino-4-phenylcyclohexyl)-4-phenoxybutyramide were obtained and, as a solution in 5 ml 2-butanone and 5 ml ethyl acetate, were converted into the corresponding hydrochloride by addition of 21.3 μl water and 150 μl chlorotrimethylsilane (420 mg of a white solid, m.p. 191-192° C.).

Example 238

N-(4-Dimethylamino-4-phenylcyclohexyl)-4-phenoxybutyramide hydrochloride, Less Polar Diastereoisomer As described for Example 237, 575 mg of the less polar diastereoisomer of N-(4-dimethylamino-4-phenylcyclohexyl)-4-phenoxybutyramide were also obtained and, as a solution in 5 ml 2-butanone and 5 ml ethyl acetate, were converted into the corresponding hydrochloride by addition of 27.2 μl water and 190 μl chlorotrimethylsilane (530 mg of a white solid, m.p. 194-197° C.).

Investigations of the activity of the compounds according to the invention:

Measurement of the ORL1 Binding

The cyclohexane derivatives of the general formula I were investigated in a receptor binding assay with $^3$H-nociceptin/orphanin FQ with membranes from recombinant CHO-ORL1 cells. This test system was conducted in accordance with the method described by Ardati et al. (Mol. Pharmacol., 51, 1997, p. 816-824). The concentration of $^3$H-nociceptin/orphanin FQ in these experiments was 0.5 nM. The binding assays were carried out with in each case 20 μg of membrane protein per 200 μl batch in 50 mM hepes, pH 7.4, 10 mM MgCl$_2$ and 1 mM EDTA. The binding to the ORL1 receptor was determined using in each case 1 mg WGA-SPA beads (Amersham-Pharmacia, Freiburg) by incubation of the batch for one hour at RT and subsequent measurement in a Trilux scintillation counter (Wallac, Finland). The affinity is stated in Table 1 as the nanomolar $K_i$ value in or % inhibition at c=1 μM.

Measurement of the μ Binding

The receptor affinity for the human μ-opiate receptor was determined in a homogeneous batch in microtitre plates. For this, dilution series of the particular substituted cyclohexyl-1,4-diamine derivative to be tested were incubated in a total volume of 250 μl for 90 minutes at room temperature with a receptor membrane preparation (15-40 μg protein per 250 μl incubation batch) of CHO-K1 cells, which express the human μ-opiate receptor (RB-HOM receptor membrane preparation of NEN, Zaventem, Belgium), in the presence of 1 nmol/l of the radioactive ligand [$^3$H]-naloxone (NET719, NEN, Zaventem, Belgium) and of 1 mg WGA-SPA beads (wheat germ agglutinin SPA beads from Amersham/Pharmacia, Freiburg, Germany). 50 mmol/l Tris-HCl supplemented with 0.05 wt. % sodium azide and with 0.06 wt. % bovine serum albumin was used as the incubation buffer. 25 μmol/l naloxone was additionally added for determination of the non-specific binding. When the ninety minutes of incubation time had ended, the microtitre plates were centrifuged off at 1,000 g for 20 minutes and the radioactivity was measured in a β-counter (Microbeta-Trilux, PerkinElmer Wallac, Freiburg, Germany). The percentage displacement of the radioactive ligand from its binding to the human μ-opiate receptor at a concentration of the test substances of 1 μmol/l was determined and was stated as the percentage inhibition (% inhibition) of the specific binding. In some cases, on the basis of the percentage displacement by different concentrations of the compounds of the general formula I to be tested, IC$_{50}$ inhibitory concentrations which cause 50 per cent displacement of the radioactive ligand were calculated. By conversion by means of the Cheng-Prusoff relationship, Ki values were obtained for the test substances.

Measurement of the Serotonin Reuptake

In order to be able to carry out these in vitro studies, synaptosomes are freshly isolated from rat brain areas. In each case a so-called "P$_2$" fraction, which is prepared in accordance with the instructions of Gray and Whittaker (E. G. Gray and V. P. Whittaker (1962) J. Anat. 76, 79-88), is used. For the 5HT uptake, these vesicular particles are isolated from the medulla+pons region of male rat brains.

A detailed description of the method can be found in the literature (M. Ch. Frink, H.-H. Hennies, W. Englberger, M. Haurand and B. Wilffert (1996) Arzneim.-Forsch./Drug Res. 46 (III), 11, 1029-1036).

Measurement of the Noradrenaline Reuptake

In order to be able to carry out these in vitro studies, synaptosomes are freshly isolated from rat brain areas. In each case a so-called "P$_2$" fraction, which is prepared in accordance with the instructions of Gray and Whittaker (E. G. Gray and V. P. Whittaker (1962) J. Anat. 76, 79-88), is used. For the NA uptake, these vesicular particles are isolated from the hypothalamus of male rat brains.

A detailed description of the method can be found in the literature (M. Ch. Frink, H.-H. Hennies, W. Englberger, M. Haurand and B. Wilffert (1996) Arzneim.-Forsch./Drug Res. 46 (III), 11, 1029-1036).

The following binding data were determined by way of example:

| Compound | μ-Opiate receptor [1 μM], % inhibition |
|---|---|
| Example 1 | 106 |
| Example 2 | 104 |
| Example 3 | 101 |
| Example 4 | 100 |
| Example 5 | 100 |
| Example 6 | 99 |
| Example 7 | 98 |
| Example 8 | 98 |
| Example 9 | 98 |
| Example 10 | 97 |
| Example 11 | 97 |
| Example 12 | 97 |
| Example 13 | 96 |
| Example 14 | 96 |
| Example 15 | 96 |
| Example 16 | 96 |
| Example 17 | 95 |
| Example 18 | 95 |
| Example 19 | 95 |
| Example 20 | 94 |
| Example 21 | 94 |
| Example 22 | 93 |
| Example 23 | 93 |
| Example 24 | 92 |
| Example 25 | 91 |
| Example 26 | 91 |
| Example 27 | 90 |
| Example 28 | 89 |
| Example 29 | 89 |
| Example 30 | 89 |
| Example 31 | 89 |
| Example 32 | 86 |
| Example 33 | 86 |
| Example 34 | 85 |
| Example 35 | 85 |
| Example 36 | 85 |
| Example 37 | 84 |
| Example 38 | 84 |
| Example 39 | 84 |
| Example 40 | 82 |
| Example 41 | 82 |
| Example 42 | 82 |
| Example 43 | 82 |

| Compound | μ-Opiate receptor [1 μM], % inhibition |
|---|---|
| Example 44 | 81 |
| Example 45 | 81 |
| Example 46 | 80 |
| Example 47 | 80 |
| Example 48 | 80 |
| Example 49 | 79 |
| Example 50 | 79 |
| Example 51 | 79 |
| Example 52 | 79 |
| Example 53 | 77 |
| Example 54 | 77 |
| Example 55 | 77 |
| Example 56 | 77 |
| Example 57 | 77 |
| Example 58 | 76 |
| Example 59 | 76 |
| Example 60 | 76 |
| Example 61 | 75 |
| Example 62 | 74 |
| Example 63 | 73 |
| Example 64 | 73 |
| Example 65 | 73 |
| Example 66 | 73 |
| Example 67 | 71 |
| Example 68 | 71 |
| Example 69 | 71 |
| Example 70 | 71 |
| Example 71 | 70 |
| Example 72 | 69 |
| Example 73 | 69 |
| Example 74 | 69 |
| Example 75 | 69 |
| Example 76 | 69 |
| Example 77 | 68 |
| Example 78 | 68 |
| Example 79 | 67 |
| Example 80 | 67 |
| Example 81 | 66 |
| Example 82 | 66 |
| Example 83 | 65 |
| Example 84 | 65 |
| Example 85 | 64 |
| Example 86 | 64 |
| Example 87 | 64 |
| Example 88 | 63 |
| Example 89 | 63 |
| Example 90 | 63 |
| Example 91 | 63 |
| Example 92 | 63 |
| Example 93 | 61 |
| Example 94 | 61 |
| Example 95 | 61 |
| Example 96 | 61 |
| Example 97 | 58 |
| Example 98 | 57 |
| Example 99 | 57 |
| Example 100 | 57 |
| Example 101 | 57 |
| Example 102 | 56 |
| Example 103 | 56 |
| Example 104 | 56 |
| Example 105 | 56 |
| Example 106 | 55 |
| Example 107 | 55 |
| Example 108 | 55 |
| Example 109 | 55 |
| Example 110 | 55 |
| Example 111 | 54 |
| Example 112 | 54 |
| Example 113 | 52 |
| Example 114 | 52 |
| Example 115 | 52 |
| Example 116 | 51 |
| Example 117 | 51 |
| Example 118 | 51 |
| Example 119 | 50 |
| Example 120 | 49 |
| Example 121 | 49 |
| Example 122 | 49 |
| Example 123 | 49 |
| Example 124 | 48 |
| Example 125 | 48 |
| Example 126 | 48 |
| Example 127 | 47 |
| Example 128 | 47 |
| Example 129 | 47 |
| Example 130 | 46 |
| Example 131 | 45 |
| Example 132 | 45 |
| Example 133 | 45 |
| Example 134 | 44 |
| Example 135 | 44 |
| Example 136 | 44 |
| Example 137 | 44 |
| Example 138 | 44 |
| Example 139 | 43 |
| Example 140 | 43 |
| Example 141 | 43 |
| Example 142 | 42 |
| Example 143 | 41 |
| Example 144 | 41 |
| Example 145 | 41 |
| Example 146 | 41 |
| Example 235 | 68 |
| Example 236 | 100 |
| Example 237 | 71 |
| Example 238 | 100 |

| Compound | ORL1 [1 μM], % inhibition |
|---|---|
| Example 1 | 44 |
| Example 3 | 64 |
| Example 4 | 78 |
| Example 6 | 93 |
| Example 7 | 84 |
| Example 8 | 88 |
| Example 9 | 60 |
| Example 10 | 62 |
| Example 11 | 82 |
| Example 12 | 97 |
| Example 17 | 96 |
| Example 19 | 99 |
| Example 20 | 93 |
| Example 23 | 91 |
| Example 25 | 70 |
| Example 26 | 63 |
| Example 44 | 56 |
| Example 53 | 50 |
| Example 65 | 43 |
| Example 78 | 52 |
| Example 235 | 46 |
| Example 236 | 99 |
| Example 237 | 39 |
| Example 238 | 99 |

| Example | 5HT uptake [10 μM], % inhibition |
|---|---|
| 236 | 97 |
| 237 | 78 |
| 238 | 98 |

| Example | NA uptake [10 µM], % inhibition |
|---|---|
| 235 | 40 |
| 236 | 87 |
| 237 | 56 |
| 238 | 77 |

Parenteral Solution of a Substituted cyclohexyl-1,4-diamine Derivative According to the Invention 38 g of one of the substituted cyclohexyl-1,4-diamine derivatives according to the invention, here Example 1, are dissolved in 1 l of water for injection purposes at room temperature and the solution is then adjusted to isotonic conditions by addition of anhydrous glucose for injection purposes.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A cyclohexyl-1,4-diamine compound corresponding to formula I

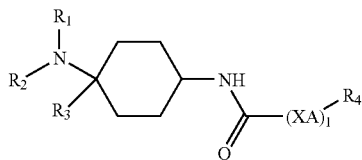

wherein $R^1$ and $R^2$, independently of one another, represent $C_{1-5}$-alkyl, in each case saturated, branched or unbranched, mono- or polysubstituted or unsubstituted; $C_{3-8}$-cycloalkyl, in each case mono- or polysubstituted or unsubstituted; or aryl, $C_{3-8}$-cycloalkyl or heteroaryl bonded via $C_{1-3}$-alkyl and in each case mono- or polysubstituted or unsubstituted; or $R^1$ and $R^2$ together form a ring and represent $CH_2CH_2OCH_2CH_2$, $CH_2CH_2NR^{10}CH_2CH_2$ or $(CH_2)_{3-6}$, wherein $R^{10}$ denotes H; $C_{1-5}$-alkyl, in each case saturated or unsaturated, branched or unbranched, mono- or polysubstituted or unsubstituted; $C_{3-8}$-cycloalkyl, in each case mono- or polysubstituted or unsubstituted; aryl or heteroaryl, in each case mono- or polysubstituted or unsubstituted; or aryl, $C_{3-8}$-cycloalkyl or heteroaryl bonded via $C_{1-3}$-alkyl and in each case mono- or polysubstituted or unsubstituted; C(O)phenyl, C(O)heteroaryl, C(O)$C_{1-5}$-alkyl, in each case substituted or unsubstituted;

$R^3$ represents $C_{1-5}$-alkyl, in each case saturated or unsaturated, branched or unbranched, mono- or polysubstituted or unsubstituted; $C_{3-8}$-cycloalkyl, in each case mono- or polysubstituted or unsubstituted; aryl or heteroaryl, in each case unsubstituted or mono- or polysubstituted; aryl, heteroaryl or $C_{3-8}$-cycloalkyl bonded via $C_{1-3}$-alkyl and in each case unsubstituted or mono- or polysubstituted;

X represents $(CR^5R^6)_n$; aryl or heteroaryl, in each case unsubstituted or mono- or polysubstituted and in each case also bridged via a $C_{1-3}$-alkyl chain, which may be substituted; where n=0, 1, 2, 3, or 4;

A represents NH, ON, wherein the bond between N and $R^4$ is a double bond, O or S, l represents 1 or 2;

$R^4$ represents $C_{1-5}$-alkyl, in each case saturated or unsaturated, branched or unbranched, mono- or polysubstituted or unsubstituted; $C_{3-8}$-cycloalkyl, in each case mono- or polysubstituted or unsubstituted; aryl or heteroaryl, in each case mono- or polysubstituted or unsubstituted; or aryl, $C_{3-8}$-cycloalkyl or heteroaryl bonded via $C_{1-3}$-alkyl and in each case mono- or polysubstituted or unsubstituted;

$R^5$ and $R^6$ independently of one another represent H, $Cl_{1-5}$-alkyl, in each case saturated or unsaturated, branched or unbranched, mono- or polysubstituted or unsubstituted; aryl, in each case mono- or polysubstituted or unsubstituted, wherein with respect to the above alkyl groups the term mono- or polysubstituted means replacement of one or more hydrogens with a substituent independently selected from the group consisting of F, Cl, Br, I, —CN, =O, =S, $NH_2$, NH-alkyl, NH-aryl, NH-heteroaryl, NH-cycloalkyl, NH-alkyl-aryl, NH-alkyl-heteroaryl, NH-alkyl-OH, N(alkyl)$_2$, N(alkyl-aryl)$_2$, N(alkyl-heteroaryl)$_2$, N(cycloalkyl)$_2$, N(alkyl-OH)$_2$, NH(C=O)alkyl, NH(C=O)aryl, $NO_2$, SH, S-alkyl, S-aryl, S-heteroaryl, S-alkyl-aryl, S-alkyl-heteroaryl, S-cycloalkyl, S-alkyl-OH, S-alkyl-SH, OH, O-alkyl, O-aryl, O-heteroaryl, O-alkyl-aryl, O-alkyl-heteroaryl, O-cycloalkyl, O-alkyl-OH, CHO, C(=O)$C_{1-6}$-alkyl, C(=S)$C_{1-6}$-alkyl, C(=O)aryl, C(=S)aryl, C(=O)$C_{1-6}$-alkyl-aryl, C(=S)$C_{1-6}$-alkyl-aryl, C(=O)-heteroaryl, C(=S)-heteroaryl, C(=O)-cycloalkyl, C(=S)-cycloalkyl, $CO_2H$, $CO_2$-alkyl, $CO_2$-alkyl-aryl, C(=O)$NH_2$, C(=O)NH-alkyl, C(=O)NHaryl, C(=O)NH-cycloalkyl, C(=O)N(alkyl)$_2$, C(=O)N(alkyl-aryl)$_2$, C(=O)N(alkyl-heteroaryl)$_2$, C(=O)N(cycloalkyl)$_2$, SO-alkyl, $SO_2$-alkyl, $SO_2NH_2$, $SO_3H$, PO(O—$C_{1-6}$-alkyl)$_2$, cycloalkyl, aryl and heteroaryl, wherein with respect to the above aryl, heteroaryl, or cycloalkyl groups, the term mono- or polysubstituted means replacement of one or more hydrogens with a substituent independently selected from the group consisting of F, Cl, Br, I, CN, $NH_2$, NH-alkyl, NH-aryl, NH-heteroaryl, NH-alkyl-aryl, NH-alkyl-heteroaryl, NH-cycloalkyl, NH-alkyl-OH, N(alkyl)$_2$, N(alkyl-aryl)$_2$, N(alkyl-heteroaryl)$_2$, N(cycloalkyl)$_2$, N(alkyl-OH)$_2$, $NO_2$, SH, S-alkyl, S-cycloalkyl, S-aryl, S-heteroaryl, S-alkyl-aryl, S-alkyl-heteroaryl, S-cycloalkyl, S-alkyl-OH, S-alkyl-SH, OH, O-alkyl, O-cycloalkyl, O-aryl, O-heteroaryl, O-alkyl-aryl, O-alkyl-heteroaryl, O-cycloalkyl, O-alkyl-OH, CHO, C(=O)$C_{1-6}$-alkyl, C(=S)$C_{1-6}$-alkyl, C(=O)aryl, C(=S)aryl, C(=O)—$C_{1-6}$-alkyl-aryl, C(=S)$C_{1-6}$-alkyl-aryl, C(=O)-heteroaryl, C(=S)-heteroaryl, C(=O)-cycloalkyl, C(=S)-cycloalkyl, $CO_2H$, $CO_2$-alkyl, $CO_2$-alkyl-aryl, C(=O)$NH_2$, C(=O)NH-alkyl C(=O)NHaryl, C(=O)NH-cycloalkyl, C(=O)N(alkyl)$_2$, C(=O)N(alkyl-aryl)$_2$, C(=O)N(alkyl-heteroaryl)$_2$, C(=O)N(cycloalkyl)$_2$, S(O)-alkyl, S(O)-aryl, $SO_2$-alkyl, $SO_2$-aryl, $SO_2NH_2$, $SO_3H$, $CF_3$, =O, =S; —O—$CH_2$—$CH_2$—O—; alkyl, cycloalkyl, aryl and heteroaryl provided if l represents 1 and A represents O or S, then X is not heteroaryl;

or a physiologically acceptable salt thereof.

2. The cyclohexyl-1,4-diamine compound of claim 1, wherein said compound is present in the form of a pure enantiomer or pure diastereoisomer.

3. The cyclohexyl-1,4-diamine compound of claim 1, wherein said compound is present in the form of a mixture of stereoisomers.

4. The cyclohexyl-1,4-diamine compound of claim 1, wherein said compound is present in the form of a racemic mixture.

5. The cyclohexyl-1,4-diamine compound according to claim 1, wherein
  $R^1$ and $R^2$ independently of one another represent $C_{1-5}$-alkyl, saturated, branched or unbranched, mono- or polysubstituted or unsubstituted; or
  $R^1$ and $R^2$ together form a ring and represent $CH_2CH_2OCH_2CH_2$, $CH_2CH_2NR^{10}CH_2CH_2$ or $(CH_2)_{3-6}$.

6. The cyclohexyl-1,4-diamine compound of claim 1, wherein $R^1$ and $R^2$ independently of one another represent $CH_3$ or $R^1$ and $R^2$ represent $CH_2CH_2OCH_2CH_2$, $(CH_2)_4$ or $(CH_2)_5$.

7. The cyclohexyl-1,4-diamine compound according to claim 1, wherein
  $R^3$ represents cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl, in each case unsubstituted or mono- or polysubstituted; $C_{5-6}$-cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bonded via a saturated, unbranched $C_{1-2}$-alkyl group and in each case unsubstituted or mono- or polysubstituted.

8. The cyclohexyl-1,4-diamine compound according to claim 1, wherein
  $R^3$ represents phenyl, furyl, thiophenyl, naphthyl, benzyl, benzofuranyl, indolyl, indanyl, benzodioxanyl, benzodioxolanyl, pyridyl, pyrimidyl, pyrazinyl or benzothiophenyl, in each case unsubstituted or mono- or polysubstituted; phenyl, furyl or thiophenyl bonded via a saturated, unbranched $C_{1-2}$-alkyl group and in each case unsubstituted or mono- or polysubstituted.

9. The cyclohexyl-1,4-diamine compound according to claim 1, wherein
  $R^3$ represents phenyl, phenethyl, thiophenyl, pyridyl or benzyl, in each case substituted or unsubstituted, particularly preferably phenyl, thienyl, 4-chlorobenzyl, benzyl, 3-chlorobenzyl, 4-methylbenzyl, 2-chlorobenzyl, 4-fluorobenzyl, 3-methylbenzyl, 2-methylbenzyl, 3-fluorobenzyl, 2-fluorobenzyl or phenethyl.

10. The cyclohexyl-1,4-diamine compound according to claim 1, wherein
  $R^4$ represents $C_{1-5}$-alkyl, cyclohexyl, cyclopentyl, cyclobutyl, cycloheptyl, cyclooctyl, phenyl, benzyl, naphthyl, anthracenyl, thiophenyl, benzothiophenyl, furanyl, isothiazolyl, imidazolyl, triazolyl, triazinyl, pyrazolyl, benzofuranyl, benzodioxolanyl, isoquinolinyl, phthalazinyl, benzo[1,2,5]thiadiazolyl, benzothiazolyl, benzotriazolyl, quinolinyl, carbazolyl, isoxazolyl, oxazolyl, indolyl, indanyl, benzodioxanyl, indazolyl, benzimidazolyl, pyrrolyl, pyridyl, pyrimidyl or pyrazinyl, in each case unsubstituted or mono- or polysubstituted; phenyl, naphthyl, anthracenyl, thiophenyl, benzothiophenyl, pyridyl, furyl, benzofuranyl, indolyl, indanyl, benzodioxanyl, pyrrolyl, pyrimidyl or pyrazinyl bonded via a saturated, unbranched substituted or unsubstituted $C_{1-2}$-alkyl group and in each case unsubstituted or mono- or polysubstituted.

11. The cyclohexyl-1,4-diamine compound according to claim 1, wherein
  $R^4$ represents $C_{1-5}$-alkyl, branched or unbranched, saturated or unsaturated, cyclohexyl, cyclopentyl, phenyl, benzyl, naphthyl, thiophenyl, benzothiophenyl, furanyl, pyrazolyl, benzofuranyl, isoquinolinyl, benzothiazolyl, benzotriazolyl, quinolinyl, isoxazolyl, oxazolyl, indolyl, pyrrolyl, pyridyl, pyrimidyl or pyrazinyl, in each case unsubstituted or mono- or polysubstituted, C(O)phenyl, benzyl or phenethyl, in each case unsubstituted or mono- or polysubstituted.

12. The cyclohexyl-1,4-diamine compound according to claim 1, wherein
  $R^4$ represents phenyl, C(O)phenyl, $C_{1-5}$-alkyl, branched or unbranched, saturated or unsaturated, benzyl, pyridyl, pyrimidinyl or indolyl, in each case unsubstituted or mono- or polysubstituted.

13. The cyclohexyl-1,4-diamine compound according to claim 1, wherein
  X represents $(CR^5R^6)_n$, phenyl, pyridyl, naphthyl, thiophenyl, furyl, pyrimidinyl or indolyl, in each case unsubstituted or mono- or polysubstituted and in each case also bridged via a $C_{1-3}$-alkyl chain, which can be substituted; where n=0, 1, 2, 3 or 4 and
  $R^5$ and $R^6$, independently of one another, represent H, $C_{1-5}$-alkyl, in each case saturated or unsaturated, branched or unbranched, mono- or polysubstituted or unsubstituted; phenyl, mono- or polysubstituted or unsubstituted.

14. The cyclohexyl-1,4-diamine compound according to claim 1, wherein
  X represents vinylbenzyl, $C_{1-5}$-alkyl, branched or unbranched, saturated or unsaturated, phenethyl, phenyl, benzyl or pyridyl, in each case unsubstituted or mono- or polysubstituted.

15. The cyclohexyl-1,4-diamine compound according to claim 1, wherein said compound is selected from the group consisting of:
  benzoic acid 2-[4-dimethylamino-4-(3-methyl-benzyl)-cyclohexylcarbamoyl]-benzyl ester;
  4-chloro-N-(2-{4-[1-(4-dimethylamino-4-phenyl-cyclohexylcarbamoyl)-1-methyl-ethoxy]-phenyl}-ethyl)-benzamide;
  N-(4-dimethylamino-4-thiophen-2-yl-cyclohexyl)-2-(2-methoxy-ethoxy)-acetamide;
  acetic acid (4-dimethylamino-4-thiophen-2-yl-cyclohexylcarbamoyl)-phenyl-methyl ester;
  benzoic acid 2-[4-(3-chloro-benzyl)-4-dimethylamino-cyclohexylcarbamoyl]-benzyl ester;
  acetic acid [4-dimethylamino-4-(3-fluoro-phenyl)-cyclohexylcarbamoyl]-phenyl-methyl ester;
  N-[4-dimethylamino-4-(3-fluoro-phenyl)-cyclohexyl]-2-phenoxy-benzamide;
  benzoic acid 2-[4-dimethylamino-4-(3-fluoro-phenyl)-cyclohexylcarbamoyl]-benzyl ester;
  benzoic acid 2-[4-dimethylamino-4-(3-fluoro-benzyl)-cyclohexylcarbamoyl]-benzyl ester;
  benzoic acid 2-(4-benzyl-4-dimethylamino-cyclohexylcarbamoyl)-benzyl ester;
  benzoic acid 2-(4-dimethylamino-4-phenyl-cyclohexylcarbamoyl)-benzyl ester;
  2-(3-chloro-phenoxy)-N-(4-dimethylamino-4-phenyl-cyclohexyl)-acetamide;
  N-[4-dimethylamino-4-(2-fluoro-benzyl)-cyclohexyl]-2-(4-methoxy-phenoxy)-5-nitro-benzamide;

benzoic acid 2-[4-dimethylamino-4-(2-fluoro-benzyl)-cyclohexylcarbamoyl]-benzyl ester;
benzoic acid 2-(4-dimethylamino-4-phenethyl-cyclohexylcarbamoyl)-benzyl ester;
benzoic acid 2-[4-dimethylamino-4-(4-methyl-benzyl)-cyclohexylcarbamoyl]-benzyl ester;
2-benzylsulfanyl-N-(4-dimethylamino-4-thiophen-2-yl-cyclohexyl)-acetamide;
benzoic acid 2-[4-dimethylamino-4-(4-fluoro-benzyl)-cyclohexylcarbamoyl]-benzyl ester;
N-(4-dimethylamino-4-phenyl-cyclohexyl)-4-phenoxy-butyramide;
N-(4-dimethylamino-4-thiophen-2-yl-cyclohexyl)-2-phenoxy-acetamide;
benzoic acid 2-(4-benzyl-4-pyrrolidin-1-yl-cyclohexylcarbamoyl)-benzyl ester;
N-[4-dimethylamino-4-(3-methyl-benzyl)-cyclohexyl]-2-phenoxy-acetamide;
4-[4-dimethylamino-4-(3-fluoro-phenyl)-cyclohexylcarbamoyl]-butyric acid methyl ester;
benzoic acid 2-[4-(4-chloro-benzyl)-4-dimethylamino-cyclohexylcarbamoyl]-benzyl ester;
N-(4-dimethylamino-4-phenyl-cyclohexyl)-2-(2-methoxy-ethoxy)-acetamide;
5-(2,5-dimethyl-phenoxy)-2,2-dimethyl-pimelic acid [4-dimethylamino-4-(3-fluoro-phenyl)-cyclohexyl]-amide;
benzoic acid 2-[4-(2-chloro-benzyl)-4-dimethylamino-cyclohexylcarbamoyl]-benzyl ester;
4-{1-[4-(2-chloro-benzyl)-4-dimethylamino-cyclohexylcarbamoyl]-1-methyl-ethoxy}-benzamide;
N-[4-(2-chloro-benzyl)-4-dimethylamino-cyclohexyl]-2-(2-chloro-phenoxy)-2-methyl-propionamide;
2-(2-chloro-phenoxy)-N-[4-dimethylamino-4-(4-fluoro-benzyl)-cyclohexyl]-2-methyl-propionamide;
N-[4-dimethylamino-4-(3-fluoro-benzyl)-cyclohexyl]-2-(4-methoxy-phenoxy)-5-nitro-benzamide;
N-[4-(2-chloro-benzyl)-4-dimethylamino-cyclohexyl]-2-phenoxy-acetamide;
N-[4-dimethylamino-4-(3-methyl-benzyl)-cyclohexyl]-2-(4-methoxy-phenoxy)-5-nitro-benzamide;
N-[4-dimethylamino-4-(2-methyl-benzyl)-cyclohexyl]-2-phenoxy-benzamide;
2-(4-chloro-phenoxy)-N-[4-dimethylamino-4-(2-fluoro-benzyl)-cyclohexyl]-acetamide;
N-[4-dimethylamino-4-(2-methyl-benzyl)-cyclohexyl]-2-phenoxy-acetamide;
N-[4-dimethylamino-4-(3-fluoro-benzyl)-cyclohexyl]-2-phenoxy-acetamide;
2-(3-chloro-phenoxy)-N-(4-dimethylamino-4-phenethyl-cyclohexyl)-acetamide;
2-(3-chloro-phenoxy)-N-[4-dimethylamino-4-(2-fluoro-benzyl)-cyclohexyl]-acetamide;
N-[4-(2-chloro-benzyl)-4-dimethylamino-cyclohexyl]-2-phenoxy-benzamide;
2-(2-chloro-phenoxy)-N-[4-dimethylamino-4-(2-methyl-benzyl)-cyclohexyl]-2-methyl-propionamide;
N-[4-(2-chloro-benzyl)-4-dimethylamino-cyclohexyl]-2-phenoxy-propionamide;
2-benzyloxy-N-[4-dimethylamino-4-(2-methyl-benzyl)-cyclohexyl]-acetamide;
acetic acid [4-dimethylamino-4-(3-fluoro-phenyl)-cyclohexylcarbamoyl]-methyl ester;
N-[4-dimethylamino-4-(2-fluoro-benzyl)-cyclohexyl]-2-phenoxy-butyramide;
acetic acid [4-(2-chloro-benzyl)-4-dimethylamino-cyclohexylcarbamoyl]-phenyl-methyl ester;
2-(4-chloro-phenoxy)-N-[4-dimethylamino-4-(2-methyl-benzyl)-cyclohexyl]-acetamide;
2-(3-chloro-phenoxy)-N-[4-dimethylamino-4-(3-methyl-benzyl)-cyclohexyl]-acetamide;
N-[4-dimethylamino-4-(4-fluoro-benzyl)-cyclohexyl]-2-phenoxy-benzamide;
N-[4-dimethylamino-4-(2-methyl-benzyl)-cyclohexyl]-2-phenoxy-propionamide;
2-benzyloxy-N-[4-(2-chloro-benzyl)-4-dimethylamino-cyclohexyl]-acetamide;
N-[4-(3-chloro-benzyl)-4-dimethylamino-cyclohexyl]-2-(3-chloro-phenoxy)-acetamide;
acetic acid (4-dimethylamino-4-thiophen-2-yl-cyclohexylcarbamoyl)-methyl ester;
2-benzylsulfanyl-N-[4-dimethylamino-4-(4-methyl-benzyl)-cyclohexyl]-acetamide;
N-[4-dimethylamino-4-(4-fluoro-benzyl)-cyclohexyl]-2-phenoxy-propionamide;
N-[4-dimethylamino-4-(2-methyl-benzyl)-cyclohexyl]-4-phenoxy-butyramide;
N-[4-(3-chloro-benzyl)-4-dimethylamino-cyclohexyl]-2-(4-methoxy-phenoxy)-5-nitro-benzamide;
benzoic acid 2-(4-benzyl-4-piperidin-1-yl-cyclohexylcarbamoyl)-benzyl ester;
N-[4-(2-chloro-benzyl)-4-dimethylamino-cyclohexyl]-2-phenoxy-butyramide;
acetic acid [4-dimethylamino-4-(2-methyl-benzyl)-cyclohexylcarbamoyl]-phenyl-methyl ester;
N-[4-dimethylamino-4-(2-fluoro-benzyl)-cyclohexyl]-2-phenoxy-acetamide;
acetic acid (4-benzyl-4-piperidin-1-yl-cyclohexylcarbamoyl)-phenyl-methyl ester;
N-[4-dimethylamino-4-(2-fluoro-benzyl)-cyclohexyl]-2-phenoxy-propionamide;
2-benzylsulfanyl-N-[4-(3-chloro-benzyl)-4-dimethylamino-cyclohexyl]-acetamide;
N-[4-dimethylamino-4-(3-fluoro-phenyl)-cyclohexyl]-2-methoxy-acetamide;
N-[4-dimethylamino-4-(3-methyl-benzyl)-cyclohexyl]-2-phenylamino-benzamide;
2-benzylsulfanyl-N-[4-dimethylamino-4-(3-methyl-benzyl)-cyclohexyl]-acetamide;
N-(4-benzyl-4-dimethylamino-cyclohexyl)-2-(4-chloro-phenoxy)-acetamide;
2-benzyloxy-N-[4-(3-chloro-benzyl)-4-dimethylamino-cyclohexyl]-acetamide;
2-benzyloxy-N-[4-dimethylamino-4-(4-methyl-benzyl)-cyclohexyl]-acetamide;
N-[4-(3-chloro-benzyl)-4-dimethylamino-cyclohexyl]-2-phenoxy-propionamide;
N-[4-(3-chloro-benzyl)-4-dimethylamino-cyclohexyl]-2-phenoxy-acetamide;
2-benzylsulfanyl-N-[4-(4-chloro-benzyl)-4-dimethylamino-cyclohexyl]-acetamide;
4-{1-[4-dimethylamino-4-(4-fluoro-benzyl)-cyclohexylcarbamoyl]-1-methyl-ethoxy}-benzamide;
N-[4-dimethylamino-4-(2-methyl-benzyl)-cyclohexyl]-2-phenoxy-butyramide;
2-(4-chloro-phenoxy)-N-[4-dimethylamino-4-(3-fluoro-benzyl)-cyclohexyl]-acetamide;
acetic acid (4-dimethylamino-4-phenethyl-cyclohexylcarbamoyl)-methyl ester;
N-[4-dimethylamino-4-(4-fluoro-benzyl)-cyclohexyl]-4-phenoxy-butyramide;
4-{1-[4-dimethylamino-4-(2-methyl-benzyl)-cyclohexylcarbamoyl]-1-methyl-ethoxy}-benzamide;

benzoic acid 2-[2-(4-dimethylamino-4-phenethyl-cyclohexylcarbamoyl)-ethyl]-phenyl ester;
acetic acid (4-benzyl-4-dimethylamino-cyclohexylcarbamoyl)-phenyl-methyl ester;
N-[4-(2-chloro-benzyl)-4-dimethylamino-cyclohexyl]-2-(4-chloro-phenoxy)-acetamide;
N-(4-benzyl-4-dimethylamino-cyclohexyl)-4-phenoxy-butyramide;
N-[4-(4-chloro-benzyl)-4-dimethylamino-cyclohexyl]-2-(4-methoxy-phenoxy)-5-nitro-benzamide;
2-(4-chloro-phenoxy)-N-[4-dimethylamino-4-(3-methyl-benzyl)-cyclohexyl]-acetamide;
N-[4-(3-chloro-benzyl)-4-dimethylamino-cyclohexyl]-2-phenylamino-benzamide;
acetic acid [4-dimethylamino-4-(3-methyl-benzyl)-cyclohexylcarbamoyl]-phenyl-methyl ester;
acetic acid 1-[4-dimethylamino-4-(2-methyl-benzyl)-cyclohexylcarbamoyl]-ethyl ester;
N-(4-benzyl-4-pyrrolidin-1-yl-cyclohexyl)-2-(4-chloro-phenoxy)-acetamide;
N-(4-phenyl-4-piperidin-1-yl-cyclohexyl)-2-(5-trifluoromethyl-pyridin-2-ylsulfanyl)-acetamide;
acetic acid [4-dimethylamino-4-(2-fluoro-benzyl)-cyclohexylcarbamoyl]-phenyl-methyl ester;
2-(3-chloro-phenoxy)-N-[4-dimethylamino-4-(3-fluoro-benzyl)-cyclohexyl]-acetamide;
N-(4-benzyl-4-dimethylamino-cyclohexyl)-2-phenoxy-propionamide;
N-[4-dimethylamino-4-(2-fluoro-benzyl)-cyclohexyl]-2-(5-trifluoromethyl-pyridin-2-ylsulfanyl)-acetamide;
4-(4-chloro-2-methyl-phenoxy)-N-(4-dimethylamino-4-phenethyl-cyclohexyl)-butyramide;
acetic acid [4-dimethylamino-4-(3-fluoro-benzyl)-cyclohexylcarbamoyl]-phenyl-methyl ester;
N-(4-dimethylamino-4-phenethyl-cyclohexyl)-4-phenoxy-butyramide;
N-[4-dimethylamino-4-(3-fluoro-benzyl)-cyclohexyl]-2-phenoxy-propionamide;
2-phenoxy-N-(4-phenyl-4-piperidin-1-yl-cyclohexyl)-butyramide;
4-(4-chloro-2-methyl-phenoxy)-N-[4-dimethylamino-4-(3-methyl-benzyl)-cyclohexyl]-butyramide;
N-[4-dimethylamino-4-(3-fluoro-benzyl)-cyclohexyl]-2-phenoxy-butyramide;
N-[4-dimethylamino-4-(2-fluoro-benzyl)-cyclohexyl]-2-methylsulfanyl-acetamide;
N-[4-(4-chloro-benzyl)-4-dimethylamino-cyclohexyl]-2-phenoxy-propionamide;
2-(4-chloro-phenoxy)-N-[4-dimethylamino-4-(4-methyl-benzyl)-cyclohexyl]-acetamide;
acetic acid [4-(3-chloro-benzyl)-4-dimethylamino-cyclohexylcarbamoyl]-phenyl-methyl ester;
N-[4-dimethylamino-4-(3-fluoro-benzyl)-cyclohexyl]-2-methylsulfanyl-acetamide;
acetic acid 1-(4-benzyl-4-dimethylamino-cyclohexylcarbamoyl)-ethyl ester;
N-[4-dimethylamino-4-(4-fluoro-benzyl)-cyclohexyl]-2-phenoxy-butyramide;
4-(4-chloro-2-methyl-phenoxy)-N-[4-dimethylamino-4-(4-methyl-benzyl)-cyclohexyl]-butyramide;
N-[4-dimethylamino-4-(3-methyl-benzyl)-cyclohexyl]-2-(5-trifluoromethyl-pyridin-2-ylsulfanyl)-acetamide;
N-(4-dimethylamino-4-phenethyl-cyclohexyl)-2-phenoxy-propionamide;
N-[4-dimethylamino-4-(2-fluoro-benzyl)-cyclohexyl]-2-ethoxy-acetamide;
N-(4-benzyl-4-dimethylamino-cyclohexyl)-2-(5-trifluoromethyl-pyridin-2-ylsulfanyl)-acetamide;
N-(4-benzyl-4-dimethylamino-cyclohexyl)-4-(4-chloro-2-methyl-phenoxy)-butyramide;
2-benzyloxy-N-[4-(4-chloro-benzyl)-4-dimethylamino-cyclohexyl]-acetamide;
benzoic acid 2-(4-azepan-1-yl-4-benzyl-cyclohexylcarbamoyl)-benzyl ester;
N-[4-(3-chloro-benzyl)-4-dimethylamino-cyclohexyl]-2-(4-chloro-phenoxy)-acetamide;
N-[4-dimethylamino-4-(4-fluoro-benzyl)-cyclohexyl]-2-phenoxy-acetamide;
N-(4-benzyl-4-piperidin-1-yl-cyclohexyl)-2-(4-chloro-phenoxy)-acetamide;
N-[4-dimethylamino-4-(4-methyl-benzyl)-cyclohexyl]-2-phenoxy-propionamide;
4-(4-benzyl-4-dimethylamino-cyclohexylcarbamoyl)-butyric acid methyl ester;
2-(4-chloro-phenoxy)-N-(4-dimethylamino-4-phenethyl-cyclohexyl)-acetamide;
acetic acid [4-dimethylamino-4-(4-methyl-benzyl)-cyclohexylcarbamoyl]-phenyl-methyl ester;
acetic acid [4-(2-chloro-benzyl)-4-dimethylamino-cyclohexylcarbamoyl]-phenyl-methyl ester;
4-chloro-N-[2-(4-{1-[4-dimethylamino-4-(3-fluoro-benzyl)-cyclohexylcarbamoyl]-1-methyl-ethoxy]-phenyl)-ethyl}-benzamide;
4-chloro-N-[2-(4-{1-[4-dimethylamino-4-(2-fluoro-benzyl)-cyclohexylcarbamoyl]-1-methyl-ethoxy}-phenyl)-ethyl]-benzamide;
N-[4-(4-chloro-benzyl)-4-dimethylamino-cyclohexyl]-4-phenoxy-butyramide;
N-(4-benzyl-4-dimethylamino-cyclohexyl)-2-(2-methoxy-ethoxy)-acetamide;
benzoic acid 2-{2-[4-dimethylamino-4-(3-methyl-benzyl)-cyclohexylcarbamoyl]-ethyl}-phenyl ester;
benzoic acid 2-[2-(4-benzyl-4-piperidin-1-yl-cyclohexylcarbamoyl)-ethyl]-phenyl ester;
N-[4-dimethylamino-4-(3-methyl-benzyl)-cyclohexyl]-2-phenoxy-nicotinamide;
acetic acid [4-dimethylamino-4-(4-fluoro-benzyl)-cyclohexylcarbamoyl]-phenyl-methyl ester;
N-(4-benzyl-4-piperidin-1-yl-cyclohexyl)-4-(4-chloro-2-methyl-phenoxy)-butyramide;
N-(4-benzyl-4-pyrrolidin-1-yl-cyclohexyl)-2-phenoxy-propionamide;
N-(4-benzyl-4-piperidin-1-yl-cyclohexyl)-2-phenoxy-acetamide;
benzoic acid 2-(4-phenyl-4-piperidin-1-yl-cyclohexylcarbamoyl)-benzyl ester;
4-[4-(3-chloro-benzyl)-4-dimethylamino-cyclohexylcarbamoyl]-butyric acid methyl ester;
benzoic acid 2-[2-(4-phenyl-4-piperidin-1-yl-cyclohexylcarbamoyl)-ethyl]-phenyl ester;
4-[4-dimethylamino-4-(4-fluoro-benzyl)-cyclohexylcarbamoyl]-butyric acid methyl ester;
acetic acid 1-(4-benzyl-4-dimethylamino-cyclohexylcarbamoyl)-1-methyl-ethyl ester;
acetic acid [4-(4-chloro-benzyl)-4-dimethylamino-cyclohexylcarbamoyl]-phenyl-methyl ester;
benzoic acid 2-{2-[4-(3-chloro-benzyl)-4-dimethylamino-cyclohexylcarbamoyl]-ethyl}-phenyl ester;
acetic acid 1-[4-dimethylamino-4-(3-fluoro-benzyl)-cyclohexylcarbamoyl]-1-methyl-ethyl ester;
N-(4-azepan-1-yl-4-benzyl-cyclohexyl)-2-phenoxy-acetamide;

4-chloro-N-(2-{4-[1-(4-dimethylamino-4-phenethyl-cyclohexylcarbamoyl)-1-methyl-ethoxy]-phenyl}-ethyl)-benzamide;
N-[4-dimethylamino-4-(2-fluoro-benzyl)-cyclohexyl]-2-isopropylideneaminooxy-propionamide;
N-[4-(3-chloro-benzyl)-4-dimethylamino-cyclohexyl]-succinic acid ethyl ester;
N-[4-dimethylamino-4-(4-fluoro-benzyl)-cyclohexyl]-2-(pyrimidin-2-ylsulfanyl)-acetamide;
acetic acid 1-[4-(4-chloro-benzyl)-4-dimethylamino-cyclohexylcarbamoyl]-1-methyl-ethyl ester;
N-[4-(4-chloro-benzyl)-4-dimethylamino-cyclohexyl]-succinic acid ethyl ester;
4-phenoxy-N-(4-phenyl-4-piperidin-1-yl-cyclohexyl)-butyramide;
N-[4-(4-chloro-benzyl)-4-dimethylamino-cyclohexyl]-2-(4-chloro-phenoxy)-acetamide;
acetic acid 1-(4-benzyl-4-piperidin-1-yl-cyclohexylcarbamoyl)-1-methyl-ethyl ester;
5-[4-dimethylamino-4-(4-methyl-benzyl)-cyclohexylcarbamoyl]-pimelic acid methyl ester;
N-[4-dimethylamino-4-(4-methyl-benzyl)-cyclohexyl]-3-methoxy-propionamide;
acetic acid 1-[4-dimethylamino-4-(3-methyl-benzyl)-cyclohexylcarbamoyl]-1-methyl-ethyl ester;
N-[4-(3-chloro-benzyl)-4-dimethylamino-cyclohexyl]-2-(2-methoxy-ethoxy)-acetamide;
N-[4-dimethylamino-4-(3-methyl-benzyl)-cyclohexyl]-4-phenoxy-butyramide;
5-[4-dimethylamino-4-(2-fluoro-benzyl)-cyclohexylcarbamoyl]-pimelic acid methyl ester;
N-(4-benzyl-4-dimethylamino-cyclohexyl)-2-methylsulfanyl-acetamide;
acetic acid 1-[4-dimethylamino-4-(4-methyl-benzyl)-cyclohexylcarbamoyl]-1-methyl-ethyl ester;
N-(4-benzyl-4-piperidin-1-yl-cyclohexyl)-2-methoxy-acetamide;
N-(4-morpholin-4-yl-4-phenyl-cyclohexyl)-succinic acid ethyl ester;
5-(2,5-dimethyl-phenoxy)-2,2-dimethyl-pimelic acid (4-azepan-1-yl-4-benzyl-cyclohexyl)-amide;
N-(4-azepan-1-yl-4-benzyl-cyclohexyl)-2-phenoxy-propionamide;
N-[4-(4-chloro-benzyl)-4-dimethylamino-cyclohexyl]-2-methylsulfanyl-acetamide;
N-[4-dimethylamino-4-(2-methyl-benzyl)-cyclohexyl]-2-methoxy-acetamide;
4-(4-chloro-2-methyl-phenoxy)-N-(4-morpholin-4-yl-4-phenyl-cyclohexyl)-butyramide;
N-[4-(3-chloro-benzyl)-4-dimethylamino-cyclohexyl]-2-methylsulfanyl-acetamide;
N-[4-dimethylamino-4-(4-methyl-benzyl)-cyclohexyl]-2-(2-methoxy-ethoxy)-acetamide;
N-(4-benzyl-4-piperidin-1-yl-cyclohexyl)-4-phenoxy-butyramide;
acetic acid 1-[4-(2-chloro-benzyl)-4-dimethylamino-cyclohexylcarbamoyl]-1-methyl-ethyl ester;
N-[4-(4-chloro-benzyl)-4-dimethylamino-cyclohexyl]-2-(2-methoxy-ethoxy)-acetamide;
N-(2-{4-[1-(4-benzyl-4-piperidin-1-yl-cyclohexylcarbamoyl)-1-methyl-ethoxy]-phenyl}-ethyl)-4-chloro-benzamide;
acetic acid 1-(4-dimethylamino-4-phenethyl-cyclohexylcarbamoyl)-ethyl ester;
N-[4-dimethylamino-4-(3-fluoro-benzyl)-cyclohexyl]-2-(2-methoxy-ethoxy)-acetamide;
N-[4-(4-chloro-benzyl)-4-dimethylamino-cyclohexyl]-2-(5-trifluoromethyl-pyridin-2-ylsulfanyl)-acetamide;
N-[4-dimethylamino-4-(4-methyl-benzyl)-cyclohexyl]-succinic acid methyl ester;
3-(4-benzyloxy-3-methoxy-phenyl)-N-(4-phenyl-4-piperidin-1-yl-cyclohexyl)-acrylamide;
N-[4-dimethylamino-4-(3-methyl-benzyl)-cyclohexyl]-2-(2-methoxy-ethoxy)-acetamide;
4-[4-dimethylamino-4-(4-methyl-benzyl)-cyclohexylcarbamoyl]-butyric acid methyl ester;
N-(4-benzyl-4-dimethylamino-cyclohexyl)-3-(4-benzyloxy-3-methoxy-phenyl)-acrylamide;
N-(4-benzyl-4-dimethylamino-cyclohexyl)-2-methoxy-acetamide;
acetic acid (4-morpholin-4-yl-4-phenyl-cyclohexylcarbamoyl)-methyl ester;
4-(4-chloro-2-methyl-phenoxy)-N-[4-dimethylamino-4-(3-fluoro-benzyl)-cyclohexyl]-butyramide;
N-(4-azepan-1-yl-4-benzyl-cyclohexyl)-2-(4-chloro-phenoxy)-acetamide;
2-phenylamino-N-(4-phenyl-4-piperidin-1-yl-cyclohexyl)-benzamide;
N-(2-{4-[1-(4-benzyl-4-pyrrolidin-1-yl-cyclohexylcarbamoyl)-1-methyl-ethoxy]-phenyl}-ethyl)-4-chloro-benzamide;
4-chloro-N-[2-(4-{1-[4-(4-chloro-benzyl)-4-dimethylamino-cyclohexylcarbamoyl]-1-methyl-ethoxy]-phenyl)-ethyl}-benzamide;
acetic acid [4-dimethylamino-4-(4-methyl-benzyl)-cyclohexylcarbamoyl]-methyl ester;
acetic acid [4-dimethylamino-4-(3-fluoro-benzyl)-cyclohexylcarbamoyl]-methyl ester;
acetic acid [4-(4-chloro-benzyl)-4-dimethylamino-cyclohexylcarbamoyl]-methyl ester;
acetic acid [4-(3-chloro-benzyl)-4-dimethylamino-cyclohexylcarbamoyl]-methyl ester;
4-[4-(4-chloro-benzyl)-4-dimethylamino-cyclohexylcarbamoyl]-butyric acid methyl ester;
acetic acid 1-(4-morpholin-4-yl-4-phenyl-cyclohexylcarbamoyl)-ethyl ester;
3-(4-benzyloxy-3-methoxy-phenyl)-N-[4-dimethylamino-4-(3-methyl-benzyl)-cyclohexyl]-acrylamide;
3-(4-benzyloxy-3-methoxy-phenyl)-N-[4-dimethylamino-4-(4-methyl-benzyl)-cyclohexyl]-acrylamide;
acetic acid [4-dimethylamino-4-(3-methyl-benzyl)-cyclohexylcarbamoyl]-methyl ester;
3-(4-benzyloxy-3-methoxy-phenyl)-N-[4-(3-chloro-benzyl)-4-dimethylamino-cyclohexyl]-acrylamide;
N-(4-morpholin-4-yl-4-phenyl-cyclohexyl)-2-phenylamino-benzamide;
N-[4-(4-chloro-benzyl)-4-dimethylamino-cyclohexyl]-2-isopropylideneaminooxy-propionamide;
4-chloro-N-(2-{4-[1-methyl-1-(4-phenyl-4-piperidin-1-yl-cyclohexylcarbamoyl)-ethoxy]-phenyl}-ethyl)-benzamide;
N-[4-(3-chloro-benzyl)-4-dimethylamino-cyclohexyl]-2-isopropylideneaminooxy-propionamide;
N-(4-morpholin-4-yl-4-phenyl-cyclohexyl)-2-(5-trifluoromethyl-pyridin-2-ylsulfanyl)-acetamide;
N-(4-phenyl-4-piperidin-1-yl-cyclohexyl)-succinic acid methyl ester;
benzoic acid 2-(4-morpholin-4-yl-4-phenyl-cyclohexylcarbamoyl)-benzyl ester;
N-[4-(3-chloro-benzyl)-4-dimethylamino-cyclohexyl]-succinic acid methyl ester;

4-chloro-N-(2-{4-[1-methyl-1-(4-morpholin-4-yl-4-phenyl-cyclohexylcarbamoyl)-ethoxy]-phenyl}-ethyl)-benzamide;
5-[4-(2-chloro-benzyl)-4-dimethylamino-cyclohexylcarbamoyl]-pimelic acid methyl ester;
4-(4-phenyl-4-piperidin-1-yl-cyclohexylcarbamoyl)-butyric acid methyl ester;
acetic acid 1-[4-dimethylamino-4-(3-methyl-benzyl)-cyclohexylcarbamoyl]-ethyl ester;
N-[4-dimethylamino-4-(3-methyl-benzyl)-cyclohexyl]-succinic acid methyl ester;
4-chloro-N-[2-(4-{1-[4-dimethylamino-4-(3-methyl-benzyl)-cyclohexylcarbamoyl]-1-methyl-ethoxy}-phenyl)-ethyl]-benzamide;
N-[4-dimethylamino-4-(2-fluoro-benzyl)-cyclohexyl]-succinic acid methyl ester;
acetic acid 1-[4-(3-chloro-benzyl)-4-dimethylamino-cyclohexylcarbamoyl]-ethyl ester;
acetic acid 1-[4-(4-chloro-benzyl)-4-dimethylamino-cyclohexylcarbamoyl]-ethyl ester;
N-(4-benzyl-4-piperidin-1-yl-cyclohexyl)-2-phenylamino-benzamide;
acetic acid 1-(4-benzyl-4-piperidin-1-yl-cyclohexylcarbamoyl)-ethyl ester;
4-chloro-N-[2-(4-{1-[4-(3-chloro-benzyl)-4-dimethylamino-cyclohexylcarbamoyl]-1-methyl-ethoxy}-phenyl)-ethyl]-benzamide;
4-chloro-N-[2-(4-{1-[4-dimethylamino-4-(4-methyl-benzyl)-cyclohexylcarbamoyl]-1-methyl-ethoxy]-phenyl)-ethyl}-benzamide;
acetic acid 1-[4-dimethylamino-4-(4-methyl-benzyl)-cyclohexylcarbamoyl]-ethyl ester;
4-[4-dimethylamino-4-(3-fluoro-benzyl)-cyclohexylcarbamoyl]-butyric acid methyl ester;
4-[4-dimethylamino-4-(3-methyl-benzyl)-cyclohexylcarbamoyl]-butyric acid methyl ester;
N-(4-morpholin-4-yl-4-phenyl-cyclohexyl)-succinic acid methyl ester;
acetic acid 1-[4-dimethylamino-4-(2-fluoro-benzyl)-cyclohexylcarbamoyl]-ethyl ester;
4-[4-dimethylamino-4-(2-fluoro-benzyl)-cyclohexylcarbamoyl]-butyric acid methyl ester;
3-(4-benzyloxy-3-methoxy-phenyl)-N-[4-dimethylamino-4-(3-fluoro-benzyl)-cyclohexyl]-acrylamide;
benzoic acid 2-{2-[4-(4-chloro-benzyl)-4-dimethylamino-cyclohexylcarbamoyl]-ethyl}-phenyl ester;
4-(4-morpholin-4-yl-4-phenyl-cyclohexylcarbamoyl)-butyric acid methyl ester;
acetic acid 1-[4-dimethylamino-4-(3-fluoro-benzyl)-cyclohexylcarbamoyl]-ethyl ester;
3-(4-benzyloxy-3-methoxy-phenyl)-N-(4-dimethylamino-4-phenethyl-cyclohexyl)-acrylamide;
N-[4-(2-chloro-benzyl)-4-dimethylamino-cyclohexyl]-2-ethoxy-acetamide;
3-(4-benzyloxy-3-methoxy-phenyl)-N-[4-(4-chloro-benzyl)-4-dimethylamino-cyclohexyl]-acrylamide;
3-(4-benzyloxy-3-methoxy-phenyl)-N-[4-dimethylamino-4-(2-fluoro-benzyl)-cyclohexyl]-acrylamide;
2-(3-chlorophenoxy)-N-(4-dimethylamino-4-phenylcyclohexyl)acetamide hydrochloride, more polar diastereoisomer;
2-(3-chlorophenoxy)-N-(4-dimethylamino-4-phenylcyclohexyl)acetamide hydrochloride, less polar diastereoisomer;
N-(4-dimethylamino-4-phenylcyclohexyl)-4-phenoxybutyramide hydrochloride, more polar diastereoisomer; and
N-(4-dimethylamino-4-phenylcyclohexyl)-4-phenoxybutyramide hydrochloride, less polar diastereoisomer.

16. A process for preparing a cyclohexyl-1,4-diamine compound according to claim 1, comprising the steps of:
linking a substituted cyclohexane-1,4-diamine with a carboxylic acid corresponding to formula II

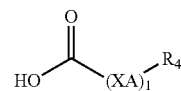

by adding coupling reagents or by activating a carboxylic acid component.

17. The process of claim 16, wherein said process comprises the step of preparing an acid chloride.

18. A pharmaceutical formulation comprising at least one cyclohexyl-1,4-diamine compound according to claim 1 and a pharmaceutically acceptable excipient.

19. A method of producing a pharmaceutical formulation comprising the step of combining a pharmaceutically effective amount of a cyclohexyl-1,4-diamine compound according to claim 1 and one or more pharmaceutically acceptable excipients.

20. A method of treating pain in a mammal, said method comprising administering to said mammal an effective amount of a compound according to claim 1.

21. The method of claim 20, wherein said pain is acute, neuropathic or chronic pain.

22. A cyclohexyl-1,4-diamine compound corresponding to formula I

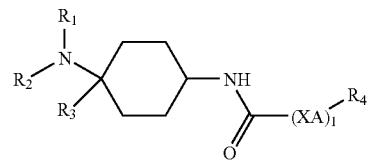

wherein $R^1$ and $R^2$, independently of one another, represent $C_{1-5}$-alkyl, in each case saturated, branched or unbranched, mono- or polysubstituted or unsubstituted; $C_{3-8}$-cycloalkyl, in each case mono- or polysubstituted or unsubstituted; or aryl, $C_{3-8}$-cycloalkyl or heteroaryl bonded via $C_{1-3}$-alkyl and in each case mono- or polysubstituted or unsubstituted; or $R^1$ and $R^2$ together form a ring and represent $CH_2CH_2OCH_2CH_2$, $CH_2CH_2NR^{10}CH_2CH_2$ or $(CH_2)_{3-6}$, wherein $R^{10}$ denotes H; $C_{1-5}$-alkyl, in each case saturated or unsaturated, branched or unbranched, mono- or polysubstituted or unsubstituted; $C_{3-8}$-cycloalkyl, in each case mono- or polysubstituted or unsubstituted; aryl or heteroaryl, in each case mono- or polysubstituted or unsubstituted; or aryl, $C_{3-8}$-cycloalkyl or heteroaryl bonded via $C_{1-3}$-alkyl and in each case mono- or polysubstituted or unsubstituted; C(O)phenyl, C(O)heteroaryl, C(O)$C_{1-5}$-alkyl, in each case substituted or unsubstituted;

$R^3$ represents $C_{1-5}$-alkyl, in each case saturated or unsaturated, branched or unbranched, mono- or polysubstituted or unsubstituted; $C_{3-8}$-cycloalkyl, in each case mono- or polysubstituted or unsubstituted; aryl or heteroaryl, in each case unsubstituted or mono- or polysubstituted; aryl, heteroaryl or $C_{3-8}$-cycloalkyl bonded via $C_{1-3}$-alkyl and in each case unsubstituted or mono- or polysubstituted;

X represents $(CR^5R^6)_n$; aryl or heteroaryl, in each case unsubstituted or mono- or polysubstituted and in each case also bridged via a $C_{1-3}$-alkyl chain, which may be substituted; where n=0, 1, 2, 3, or 4;

A represents NH, ON, wherein the bond between N and $R^4$ is a double bond, O or S, l represents 1 or 2;

$R^4$ represents $C_{1-5}$-alkyl, in each case saturated or unsaturated, branched or unbranched, mono- or polysubstituted or unsubstituted; $C_{3-8}$-cycloalkyl, in each case mono- or polysubstituted or unsubstituted; aryl or heteroaryl, in each case mono- or polysubstituted or unsubstituted; or aryl, $C_{3-8}$-cycloalkyl or heteroaryl bonded via $C_{1-3}$-alkyl and in each case mono- or polysubstituted or unsubstituted;

$R^5$ and $R^6$ independently of one another represent H, $C_{1-5}$-alkyl, in each case saturated or unsaturated, branched or unbranched, mono- or polysubstituted or unsubstituted; aryl, in each case mono- or polysubstituted or unsubstituted, provided if l represents 1 and A represents O or S, then X is not heteroaryl;

or an acid, base, solvate or physiologically acceptable salt thereof.

\* \* \* \* \*